(12) United States Patent
Landau et al.

(10) Patent No.: US 7,115,606 B2
(45) Date of Patent: *Oct. 3, 2006

(54) METHOD OF TREATING LOWER URINARY TRACT DISORDERS

(75) Inventors: Steven B. Landau, Wellesley, MA (US); Cheryl L. Miller, Natick, MA (US); Matthew O. Fraser, Apex, NC (US)

(73) Assignee: Dynogen Pharmaceuticals, Inc., Waltham, MA (US)

( * ) Notice: Subject to any disclaimer, the term of this patent is extended or adjusted under 35 U.S.C. 154(b) by 110 days.

This patent is subject to a terminal disclaimer.

(21) Appl. No.: 10/863,770

(22) Filed: Jun. 7, 2004

(65) Prior Publication Data

US 2005/0026909 A1    Feb. 3, 2005

Related U.S. Application Data

(63) Continuation of application No. 10/817,332, filed on Apr. 2, 2004, now Pat. No. 6,846,823.

(60) Provisional application No. 60/536,341, filed on Jan. 13, 2004, provisional application No. 60/496,502, filed on Aug. 20, 2003, provisional application No. 60/461,022, filed on Apr. 4, 2003.

(51) Int. Cl.
*A61K 31/496* (2006.01)
(52) U.S. Cl. .................................................. 514/249
(58) Field of Classification Search ................. 514/249
See application file for complete search history.

(56) References Cited

U.S. PATENT DOCUMENTS

| 4,695,568 | A | * | 9/1987 | Ninomiya et al. ..... 514/252.16 |
|---|---|---|---|---|
| 4,939,136 | A | | 7/1990 | Haeck et al. |
| 5,225,407 | A | | 7/1993 | Oakley et al. |
| 5,352,685 | A | | 10/1994 | Maruyama et al. |
| 5,663,343 | A | | 9/1997 | van der Meij et al. |
| 5,945,415 | A | | 8/1999 | Kato et al. |
| 5,962,494 | A | | 10/1999 | Young |
| 5,977,127 | A | | 11/1999 | Bonnacker et al. |
| 6,300,336 | B1 | | 10/2001 | Eeckhout et al. |
| 6,355,647 | B1 | | 3/2002 | Steiner et al. |
| 6,440,453 | B1 | | 8/2002 | Fischer et al. |
| 6,465,458 | B1 | | 10/2002 | Wong et al. |
| 6,846,823 | B1 | * | 1/2005 | Landau et al. .............. 514/249 |
| 2001/0020025 | A1 | | 9/2001 | Megens |
| 2002/0002167 | A1 | | 1/2002 | Mueller et al. |
| 2002/0010216 | A1 | | 1/2002 | Rogosky et al. |
| 2002/0107249 | A1 | | 8/2002 | Wong et al. |
| 2003/0158221 | A1 | | 8/2003 | Zhang et al. |
| 2003/0203055 | A1 | | 10/2003 | Rao et al. |
| 2004/0048874 | A1 | | 3/2004 | Bardsley et al. |

FOREIGN PATENT DOCUMENTS

| GB | 0216027.3 | 7/2002 |
|---|---|---|
| GB | 0220064.0 | 8/2002 |
| GB | 0304648.9 | 2/2003 |
| GB | 0316115.5 | 9/2003 |
| JP | 06016557 A2 | 1/1994 |
| WO | WO 98/50037 | 11/1998 |
| WO | WO 00/06160 A1 | 2/2000 |
| WO | WO 00/48581 A3 | 8/2000 |
| WO | WO 01/26623 A3 | 4/2001 |
| WO | WO 02/094249 A1 | 11/2002 |
| WO | WO 03/061657 A1 | 7/2003 |
| WO | WO 03/063873 A1 | 8/2003 |
| WO | WO 03/077897 A1 | 9/2003 |
| WO | WO 2004/004734 A1 | 1/2004 |
| WO | WO 2004/019948 A1 | 3/2004 |

OTHER PUBLICATIONS

Clemett, Tolterodine: a review of its use in the treatment of overactive bladder, PMID: 11341475 (2001).*
Hofner, Trospium chloride—an effective drug in the treatment of overactive bladder and detrusor hyperreflexia, World J Urol (2001) 19:336-343.*
Hunsballe, Clinical options for imipramine in the management of urinary incontinence, Urol Res (2001) 29:118-125.*
U.S. Appl. No. 10/757,981, filed Jan. 13, 2004, Landau et al.
Andersson, K. E., "Treatment of Overactive Bladder: Other Drug Mechanisms," Urology, 55(Supplement 5A):51-59 (2000).
Andersson, K.E., "Treatment of the Overactive Bladder: Possible Central Nervous System Drug Targets," Urology, 59 (Suppl 5A):18.

(Continued)

*Primary Examiner*—Amelia A. Owens
(74) *Attorney, Agent, or Firm*—Jones Day

(57) ABSTRACT

The invention relates to a method of treating at least one symptom of a lower urinary tract disorder in a subject in need of treatment wherein the symptom is selected from the group consisting of urinary frequency, urinary urgency, urinary urge incontinence, nocturia and enuresis. The method comprises administering to a subject in need of treatment a therapeutically effective amount of a compound that has 5-HT$_3$ receptor antagonist activity and NorAdrenaline Reuptake Inhibitor (NARI) activity. The invention further relates to a method of treating at least one symptom of a lower urinary tract disorder in a subject in need of treatment wherein the symptom is selected from the group consisting of urinary frequency, urinary urgency, urinary urge incontinence, nocturia and enuresis, comprising coadministering to said subject a first amount of a 5-HT$_3$ antagonist and a second amount of a NARI, wherein the first and second amounts together comprise a therapeutically effective amount or are each present in a therapeutically effective amount.

16 Claims, 2 Drawing Sheets

OTHER PUBLICATIONS

Andersson, K.E., "Bladder Activation: Afferent Mechanisms," Urology, 59 (Suppl 5A):43.

Appell, R. A. et al., "Prospective Randomized Controlled Trial of Extended-Release Oxybutynin Chloride and Tolterodine Tartrate in the Treatment of Overactive Bladder: Results of the OBJECT Study," Mayo Clin. Proc. 76:358-363 (2001).

Barras, M. et al., "Characterisation of the 5-HT Receptor Potentiating Neurotransmission in Rabbit Bladder," Eur. J. Pharmacol., 318(2-3):425-428 (1996).

Béïque, J.-C. et al., "Affinities of Venlafaxine and Various Reuptake Inhibitors for the Serotonin and Norepinephrine Transporters," Eur. J. Pharmacol., 349:129-132 (1998).

Burns, M. J., The Pharmacology and Toxicology of Reboxetine, [Retrieved from the Internet Dec. 4, 2002]. Retrieved from the Internet <http://www.ijmt.net/3_4/3_4_26.html>.

Butler, A. et al., "Pharmacological Properties of GR38032F, a Novel Antagonist at 5-HT3 Receptors," Br. J. Pharmacol., 94(2): 397-412 (1988).

Bymaster, F. P. et al., "Comparative Affinity of Duloxetine and Venlafaxine for Serotonin Norepinephrine Transporters in vitro and in vivo, Human Serotonin Receptor Subtypes, and Other Neuronal Receptors," Neuropharmacol., 25(6):871-880 (2001).

Center for Drug Evaluation and Research Application No.: 020623; Pharmacology Reviews; Jul. 5, 1996.

Chancellor, M.B., "New Frontiers in the Treatment of Overactive Bladder and Incontinence," Reviews in Urology, 4(4): S50-S56 (2002).

Chuang, Y.C. et al., "Intravesical Protamine Sulfate and Potassium Chloride as a Model for Bladder Hyperactivity," Urology, 61(3): 664.

Collins M.M. et al., "How Common is Prostatitis? A National Survey of Physician Visits," J. Urol., 159:1224-1228 (1998).

Downie, J.W., "Pharmacological Manipulation of Central Micturition Circuitry," Curr. Opin. CPNS Inves. Drugs, 1(2):231.

Eguchi, J. et al., "Pharmacological Profile of the Novel Antidepressant 4-(2-Fluorophenyl)-6-methyl-2-(1-piperazinyl)thieno-[2,3-d]pyrimidine Monohydrate Hydrochloride," Arzneim.-Forschung/Drug Res., 47(12):1337-47 (1997).

Eguchi, J. et al., "The Anxiolytic-like Effect of MCI-225, a Selective NA Reuptake Inhibitor with 5-HT3 Receptor Antagonism," Pharm., Biochem. and Behavior 68:677-683 (2001).

Elliott, D. S. et al., "Medical Management of Overactive Bladder," Mayo Clin. Proc. 76:353-355 (2001).

Elmiron® (pentosan polysulfate sodium), capsules, Product Information, Ortho-McNeil Pharmaceutical,Inc., Ranitan, N.J. (2002).

Espey, M.J. et al., "Serotonergic Modulation of Spinal Ascending Activity and Sacral Reflex Activity Evoked by Pelvic Nerve Stimulation in Cats," Brain Res., 798(1-2):101-108 (1998).

Evans, R.J., "Treatment Approaches for Interstitial Cystitis: Multimodality Therapy," Reviews in Urology, 4(Suppl. 1): S16-S20 (2002).

Fairweather, D. B. et al., "The Psychomotor and Cognitive Effects of Litoxetine in Young and Middle Aged Volunteers," Br. J. Clin. Pharmacol. 40:119-125 (1995).

Ito, C. et al., "Effect of GK-128 [2-[(2-Methylimidazol-1-yl)methyl]-benzo[f]thiochromen-1-one Monohydrocholoride Hemihydrate], a Selective 5-Hydroxytryptamine3 Receptor Antagonist, on Colonic Function in Rats," J. Pharmacol. Exp. Ther., 280(1): 67-72 (1997).

Katofiasc, M. A. et al., "Comparison of the Effects of Serotonin Selective, Norepinephrine Selective, and Dual Serotonin and Norepinephrine Reuptake Inhibitors on Lower Urinary Tract Function in Cats," Life Sci., 71:1227-1236 (2002).

Khan, M.A. et al., "Doxazosin Modifies Serotonin-Mediated Rabbit Urinary Bladder Contraction. Potential Clinical Relevance," Urol. Res., 28:116-121 (2000).

Kilpatrick, G.J. et al., "Identification and Distribution of 5-HT3 Receptors in Rat Brain Using Radioligand Binding," Nature, 330: 746-748 (1987).

Kodama, M. and Takimoto, Y., "Influence of 5-Hydroxytryptamine and the Effect of a New Serotonin Receptor Antagonist (Sarpogrelate) on Detrusor Smooth Muscle of Streptozotocin-Induced Diabetes Mellitus in the Rat," International Journal of Urology 7:231-235 (2000).

LOTRONEX (alosetron hydrochloride)—Tablets, Product Information, GlaxoSmithKline, Research Triangle Park, NC, pp. 1-13 (2002).

Metts, J. F., "Interstitial Cystitis: Urgency and Frequency Syndrome," American Family Physician, 64(7): 1199.

Morrison, J. et al., "Neurophysiology and Neuropharmacology" In: Incontinence (vol. 2) Abrams, P., Cardozo, L., Khoury, S., and Wein, A., Eds. (UK, Health Publications, Ltd.,) pp. 83.

Owens, M. J. et al., "Neurotransmitter Receptor and Transporter Binding Profile of Antidepressants and their Metabolites1," J. Pharmacol. Exp. Ther., 283(3): 1305.

Sasaki, K. et al., "Diabetic Cystopathy Correlates with a Long-Term Decrease in Nerve Growth Factor Levels in the Bladder and Lumbosacral Dorsal Root Ganglia," J. Urol., 168(3): 1259-1264 (2002).

Sharma, A. et al., "Pharmacokinetics and Safety of Duloxetine, a Dual-Serotonin and Norepinephrine Reuptake Inhibitor," J. Clin. Pharmacol., 40:161-167 (2000).

Simon, H. et al. Eds., "Benign Prostatic Hyperplasia and Lower Urinary Tract Symptoms", [Retrieved from the Internet Mar. 18, 2003]. Retrieved from the Internet <http://wellness.ucdavis.edu/medical_conditions_az/prostaticyperplasia71.html>.

Testa, R. et al., "Effect of Different 5-Hydroxytryptamine Receptor Subtype Antagonists on the Micturition Reflex in Rats," BJU Int., 87(3):256-264 (2001).

Theoharides, T. C. and Sant, G.R., "New Agents for the Medical Treatment of Interstitial Cystitis," Exp. Opin. Invest. Drugs, 10(3): 521.

Thor, K. B. et al. "Effects of Duloxetine, a Combined Serotonin and Norephinephrine Reuptake Inhibitor, on Central Neural Control of Lower Urinary Tract Function in the Chloralose-Anesthetized Female Cat," J. Pharmacol. Exp. Ther., 274: 1014-1024 (1995).

Tonini, M. et al., "Characterization of the 5-HT Receptor Potentiating Neuromuscular Cholinergic Transmission in Strips of Human Isolated Detrusor Muscle," Br. J. Pharmacol., 113(1):1-2 (1994).

Wong, E. H. F. et al., "Reboxetine: A Pharmacologically Potent, Selective, and Specific Norepinephrine Reuptake Inhibitor," Biol. Psych., 47(9):818-829 (2000).

Wood, J.D. et al. "Fundamentals of Neurogastroenterology," Gut, 45(Suppl II):II6-II16 (1999).

Yoshida, A. et al., "5-Hydroxytryptamine Receptors, Especially the 5-HT4 Receptor, in Guinea Pig Urinary Bladder," Jpn. J. Pharmacol., 89(4):349-355 (2002).

Yoshimura, N. and Chancellor, M. B., "Current and Future Pharmacological Treatment for Overactive Bladder," J. Urol., 168:1897.

* cited by examiner

METHOD OF TREATING LOWER URINARY TRACT DISORDERS

RELATED APPLICATIONS

This application is a continuation of, and claims benefit of, U.S. application Ser. No. 10/817,332, filed Apr. 2, 2004, now U.S. Pat. No. 6,846,823, which claims the benefit of U.S. Provisional Application No. 60/536,341 filed on Jan. 13, 2004, U.S. Provisional Application No. 60/496,502 filed on Aug. 20, 2003 and U.S. Provisional Application No. 60/461,022 filed on April 4, 2003, each of which is incorporated by reference in its entirety herein.

BACKGROUND OF THE INVENTION

Lower urinary tract disorders affect the quality of life of millions of men and women in the United States every year. While the kidneys filter blood and produce urine, the lower urinary tract functions to store and periodically eliminate urine and includes all other parts of the urinary tract except the kidneys. Generally, the lower urinary tract includes the ureters, the urinary bladder, sphincter and the urethra. Disorders of the lower urinary tract include overactive bladder, interstitial cystitis, prostatitis, prostadynia and benign prostatic hyperplasia.

Overactive bladder is a treatable medical condition that is estimated to affect 17 to 20 million people in the United States. Symptoms of overactive bladder can include urinary frequency, urinary urgency, urinary urge incontinence (accidental loss of urine) due to a sudden and unstoppable need to urinate, nocturia (the disturbance of nighttime sleep because of the need to urinate) or enuresis resulting from overactivity of the detrusor muscle (the smooth muscle of the bladder which contracts and causes it to empty).

Neurogenic overactive bladder (or neurogenic bladder) is a type of overactive bladder which occurs as a result of detrusor muscle overactivity referred to as detrusor hyperreflexia, secondary to known neurologic disorders. Patients with neurologic disorders, such as stroke, Parkinson's disease, diabetes, multiple sclerosis, peripheral neuropathy, or spinal cord lesions often suffer from neurogenic overactive bladder. In contrast, non-neurogenic overactive bladder occurs as a result of detrusor muscle overactivity referred to as detrusor muscle instability. Detrusor muscle instability can arise from non-neurological abnormalities, such as bladder stones, muscle disease, urinary tract infection or drug side effects or can be idiopathic.

Due to the enormous complexity of micturition (the act of urination) an exact mechanism which causes overactive bladder is not known. Overactive bladder can result from hypersensitivity of sensory neurons of the urinary bladder, arising from various factors including inflammatory conditions, hormonal imbalances, and prostate hypertrophy. Destruction of the sensory nerve fibers, either from a crushing injury to the sacral region of the spinal cord, or from a disease that causes damage to the dorsal root fibers as they enter the spinal cord can also lead to overactive bladder. In addition, damage to the spinal cord or brain stem causing interruption of transmitted signals can lead to abnormalities in micturition. Therefore, both peripheral and central mechanisms can be involved in mediating the altered activity in overactive bladder.

In spite of the uncertainty regarding whether central or peripheral mechanisms, or both, are involved in overactive bladder, many proposed mechanisms implicate neurons and pathways that mediate non-painful visceral sensation. Somatosensory information from the bladder is relayed by nociceptive A$\delta$ and C fibers that enter the spinal cord via the dorsal root ganglion (DRG) and project to the brainstem and thalamus via second or third order neurons (Andersson (2002) *Urology* 59:18–24; Andersson (2002) *Urology* 59:43–50; Morrison, J., Steers, W. D., Brading, A., Blok, B., Fry, C., de Groat, W. C., Kakizaki, H., Levin, R., and Thor, K. B., "Basic Urological Sciences" In: Incontinence (vol. 2) Abrams, P. Khoury, S., and Wein, A. (Eds.) Health Publications, Ltd., Plymbridge Ditributors, Ltd., Plymouth, UK., (2002). A number of different subtypes of sensory afferent neurons can be involved in neurotransmission from the lower urinary tract. These can be classified as, but not limited to, small diameter, medium diameter, large diameter, myelinated, unmyelinated, sacral, lumbar, peptidergic, nonpeptidergic, IB4 positive, IB4 negative, C fiber, A$\delta$ fiber, high threshold or low threshold neurons. Nociceptive input to the DRG is thought to be conveyed to the brain along several ascending pathways, including the spinothalamic, spinoreticular, spinomesencephalic, spinocervical, and in some cases dorsal column/medial lemniscal tracts (A. I. Basbaum and T. M. Jessell (2000) The perception of pain. In *Principles of Neural Science*, 4th. ed.).

Currently there are no clinically approved applications of central nervous system oriented pharmacotherapies for treating lower urinary tract disorders, such as overactive bladder. However, recent animal studies have suggested potential targets in the central nervous system for modulating urinary tract functions. For example, in the raphe nucleus of the caudal brain stem, 5-hydroxytryptamine (serotonin, 5-HT) containing neurons send projections to the dorsal horn as well as to the autonomic and sphincter motor nuclei in the lumbosacral spinal cord. The sympathetic and parasympathetic autonomic nuclei as well as the sphincter motor nuclei receive prominent serotonergic input from the raphe nuclei in the caudal brain stem. Activity in the serotonergic pathway generally enhances urine storage by facilitating the vesical sympathetic reflex pathway and inhibiting the parasympathetic voiding pathway (Sharma, A. et al. (2000) Pharmacokinetics and safety of duloxetine, a dual-serotonin and norepinephrine reuptake inhibitor. *J. Clin. Pharmacol.* 40: 161 and Thor, K. B. et al. (1995) Effects of duloxetine, a combined serotonin and norepinephrine reuptake ihibitor, on central neural control of lower urinary tract function in the chloralose-anesthetized female cat. *J. Pharmacol. Exp. Ther.* 274: 1016.)

Among the various subtypes of 5-HT receptors, 5-HT$_2$ and 5-HT$_3$ receptors mediate excitatory effects on sympathetic and somatic reflexes to increase outlet resistance. Moreover, 5-HT$_{2C}$ and 5-HT$_3$ receptors have also been shown to be involved in inhibition of the micturition reflex (Downie, J. W. (1999) Pharmacological manipulation of central micturition circuitry. *Curr. Opin. SPNS Inves. Drugs* 1:23). In fact, 5-HT$_3$ receptor inhibition has been shown to diminish 5-HT mediated contractions in rabbit detrusor (Khan, M. A. et al. (2000) Doxazosin modifies serotonin-mediated rabbit urinary bladder contraction. Potential clinical relevance. *Urol. Res.* 28:116).

Current treatments for overactive bladder include medication, diet modification, programs in bladder training, electrical stimulation, and surgery. Currently, antimuscarinics (which are members of the general class of anticholinergics) are the primary medication used for the treatment of overactive bladder. The antimuscarinic, oxbutynin, has been the mainstay of treatment for overactive bladder. However, treatment with antimuscarinics suffers from limited efficacy and side effects such as dry mouth, dry eyes, dry vagina, blurred vision, cardiac side effects, such as palpitations and arrhythmia, drowsiness, urinary retention, weight gain, hypertension and constipation, which have proven difficult for some individuals to tolerate.

Interstitial cystitis is another lower urinary tract disorder of unknown etiology that predominantly affects young and middle-aged females, although men and children can also be affected. Symptoms of interstitial cystitis can include irritative voiding symptoms, urinary frequency, urinary urgency, nocturia or suprapubic or pelvic pain related to and relieved by voiding. Many interstitial cystitis patients also experience headaches as well as gastrointestinal and skin problems. In some cases, interstitial cystitis can also be associated with ulcers or scars of the bladder.(Metts, J. F. (2001) Interstitial Cystitis: Urgency and Frequency Syndrome. *American Family Physician* 64(7): 1199–1206).

Currently, the only FDA-approved oral medication for use in interstitial cystitis is ELMIRON® (pentosan polysulfate sodium). ELMIRON® was approved in 1996 and is thought to work by restoring a damaged, thin or leaky bladder surface. However, ELMIRON® must be taken continually for several months before any improvements can be expected. As such, lack of patient compliance often results in unsuccessful treatment. In addition, treatment with ELMIRON® is not effective in a large percentage of patients.

Other medications which have been used "off-label" for the treatment of interstitial cystitis include, for example, antidepressants, antihistamines and anticonvulsants (See, Theoharides, T. C. (2001) New agents for the medical treatment of interstitial cystitis. *Exp. Opin. Invest. Drugs* 10(3): 521–46). However, in view of the unknown cause of interstitial cystitis and the suggestion that the disorder is multifactorial in origin, these additional therapies have not provided adequate relief of the associated symptoms.

Prostatitis and prostadynia are other lower urinary tract disorders that have been suggested to affect approximately 2–9% of the adult male population (Collins M. M. et al., (1998) "How common is prostatitis? A national survey of physician visits," *Journal of Urology*, 159: 1224–1228). Prostatitis is an inflammation of the prostate, and includes bacterial prostatitis (acute and chronic) and non-bacterial prostatitis. Acute and chronic bacterial prostatitis are characterized by inflammation of the prostate and bacterial infection of the prostate gland, usually associated with symptoms of pain, urinary frequency and/or urinary urgency. Chronic bacterial prostatitis is distinguished from acute bacterial prostatitis based on the recurrent nature of the disorder. Chronic non-bacterial prostatitis is characterized by inflammation of the prostate which is of unknown etiology accompanied by the presence of an excessive amount of inflammatory cells in prostatic secretions not currently associated with bacterial infection of the prostate gland, and usually associated with symptoms of pain, urinary frequency and/or urinary urgency. Prostadynia is a disorder which mimics the symptoms of prostatitis absent inflammation of the prostate, bacterial infection of the prostate and elevated levels inflammatory cells in prostatic secretions. Prostadynia can be associated with symptoms of pain, urinary frequency and/or urinary urgency.

Currently, there are no established treatments for prostatitis and prostadynia. Antibiotics are often prescribed, but with little evidence of efficacy. COX-2 selective inhibitors and α-adrenergic blockers and have been suggested as treatments, but their efficacy has not been established. Hot sitz baths and anticholinergic drugs have also been employed to provide some symptomatic relief.

Benign prostatic hyperplasia (BPH) is a non-malignant enlargement of the prostate that is very common in men over 40 years of age. BPH is thought to be due to excessive cellular growth of both glandular and stromal elements of the prostate. Symptoms of BPH can include urinary frequency, urinary urgency, urge incontinence, nocturia, or reduced urinary force and speed of flow.

Invasive treatments for BPH include transurethral resection of the prostate, transurethral incision of the prostate, balloon dilation of the prostate, prostatic stents, microwave therapy, laser prostatectomy, transrectal high-intensity focused ultrasound therapy and transurethral needle ablation of the prostate. However, complications can arise through the use of some of these treatments, including retrograde ejaculation, impotence, postoperative urinary tract infection and some urinary incontinence. Non-invasive treatments for BPH include androgen deprivation therapy and the use of 5α-reductase inhibitors and α-adrenergic blockers. However, these treatments have proven only minimally to moderately effective for some patients.

In view of the limitations associated with existing therapies and treatments for lower urinary tract disorders, new therapies and treatments are highly desirable.

SUMMARY OF THE INVENTION

The invention relates to a method of treating at least one symptom of a lower urinary tract disorder in a subject in need of treatment wherein the symptom is selected from the group consisting of urinary frequency, urinary urgency, urinary urge incontinence, nocturia and enuresis. The method comprises administering to a subject in need of treatment a therapeutically effective amount of a compound that has 5-HT$_3$ receptor antagonist activity and NorAdrenaline Reuptake Inhibitor (NARI) activity.

In a particular embodiment, the compounds having 5-HT$_3$ receptor antagonist activity and NARI activity are thieno[2,3-d]pyrimidine derivatives such as those described in U.S. Pat. No. 4,695,568, the entire content of which is incorporated herein by reference.

In a specific embodiment, the compounds having 5-HT$_3$ receptor antagonist activity and NARI activity are represented by structural Formula I:

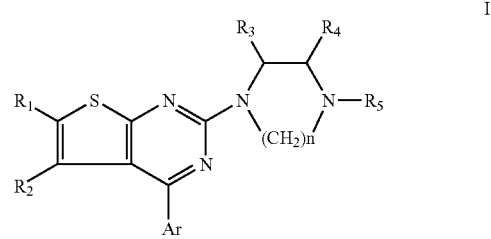

wherein, R$_1$ and R$_2$ independently represent hydrogen, halogen or a C$_1$–C$_6$ alkyl group; or R$_1$ and R$_2$ together with the carbon atoms to which they are attached form a cycloalkylene group having 5 to 6 carbon atoms;

$R_3$ and $R_4$ independently represent hydrogen or a $C_1$–$C_6$ alkyl group;

$R_5$ is hydrogen, $C_1$–$C_6$ alkyl,

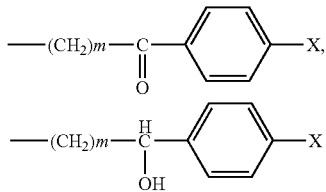

or —C(O)—NH—$R_6$, wherein m is an integer from about 1 to about 3, X is halogen and $R_6$ is a $C_1$–$C_6$ alkyl group;

Ar is a substituted or unsubstituted phenyl, 2-thienyl or 3-thienyl group; and n is 2 or 3; or a pharmaceutically acceptable salt thereof In a specific embodiment, the compound having 5-$HT_3$ receptor antagonist activity and NARI activity is represented by the formula:

II

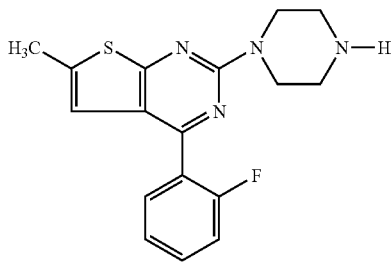

or a pharmaceutically acceptable salt thereof. This compound is commonly referred to as MCI-225, also referred to as DDP-225. The chemical name of the structure set forth in the formula is: 4-(2-fluorophenyl)-6-methyl-2-(1-piperazinyl)thieno[2,3-d]pyrimidine.

In as specific embodiment, the symptom is selected from the group consisting of urinary frequency, urinary urgency, nocturia and enuresis.

In one embodiment, the lower urinary tract disorder can be selected from the group consisting of overactive bladder, interstitial cystitis, prostatitis, prostadynia and benign prostatic hyperplasia.

In another embodiment, the lower urinary tract disorder is overactive bladder.

In yet another embodiment, the lower urinary tract disorder is interstitial cystitis.

The invention further relates to a method of treating at least one symptom of a lower urinary tract disorder in a subject in need of treatment wherein the symptom is selected from the group consisting of urinary frequency, urinary urgency, urinary urge incontinence, nocturia and enuresis comprising coadministering to said subject a therapeutically effective amount of a 5-$HT_3$ receptor antagonist and a therapeutically effective amount of a NARI.

The invention further relates to a method of treating at least one symptom of a lower urinary tract disorder in a subject in need of treatment wherein the symptom is selected from the group consisting of urinary frequency, urinary urgency, urinary urge incontinence, nocturia and enuresis comprising coadministering to said subject a first amount of a 5-$HT_3$ receptor antagonist and a second amount of a NARI, wherein the first and second amounts together comprise a therapeutically effective amount.

In as specific embodiment, the symptom is selected from the group consisting of urinary frequency, urinary urgency, nocturia and enuresis.

In one embodiment, the lower urinary tract disorder can be selected from the group consisting of overactive bladder, interstitial cystitis, prostatitis, prostadynia and benign prostatic hyperplasia.

In another embodiment, the lower urinary tract disorder is overactive bladder.

In yet another embodiment, the lower urinary tract disorder is interstitial cystitis.

The invention further relates to pharmaceutical compositions useful for the treatment of at least one symptom of a lower urinary tract disorder in a subject in need of treatment wherein the symptom is selected from the group consisting of urinary frequency, urinary urgency, urinary urge incontinence, nocturia and enuresis. The pharmaceutical composition comprises a first amount of a 5-$HT_3$ receptor antagonist compound and a second amount of a NARI compound. The pharmaceutical compositions of the present invention can optionally contain a pharmaceutically acceptable carrier. The 5-$HT_3$ receptor antagonist and the NARI can each be present in the pharmaceutical composition in a therapeutically effective amount. In another aspect, said first and second amounts can together comprise a therapeutically effective amount.

In as specific embodiment, the symptom is selected from the group consisting of urinary frequency, urinary urgency, nocturia and enuresis.

In one embodiment, the lower urinary tract disorder can be selected from the group consisting of overactive bladder, interstitial cystitis, prostatitis, prostadynia and benign prostatic hyperplasia.

In another embodiment, the lower urinary tract disorder is overactive bladder.

In yet another embodiment, the lower urinary tract disorder is interstitial cystitis.

The invention further relates to use of a compound that has 5-$HT_3$ receptor antagonist activity and NARI activity for the manufacture of a medicament for treating at least one symptom of a lower urinary tract disorder in a subject in need of treatment wherein the symptom is selected from the group consisting of urinary frequency, urinary urgency, urinary urge incontinence, nocturia and enuresis. In addition, the invention also relates to the use of a pharmaceutical composition comprising a first amount of a 5-$HT_3$ receptor antagonist compound and a second amount of a NARI compound for the manufacture of a medicament for the treatment of at least one symptom of a lower urinary tract disorder in a subject in need of treatment wherein the symptom is selected from the group consisting of urinary frequency, urinary urgency, urinary urge incontinence, nocturia and enuresis. The pharmaceutical composition used for the manufacture of a medicament can optionally contain a pharmaceutically acceptable carrier. The 5-$HT_3$ receptor antagonist and the NARI can each be present in the pharmaceutical composition in a therapeutically effective amount or said first and second amounts can together comprise a therapeutically effective amount.

The foregoing and other objects, features and advantages of the invention will be apparent from the following more particular description of preferred embodiments of the invention.

DETAILED DESCRIPTION OF THE INVENTION

Figure 1:
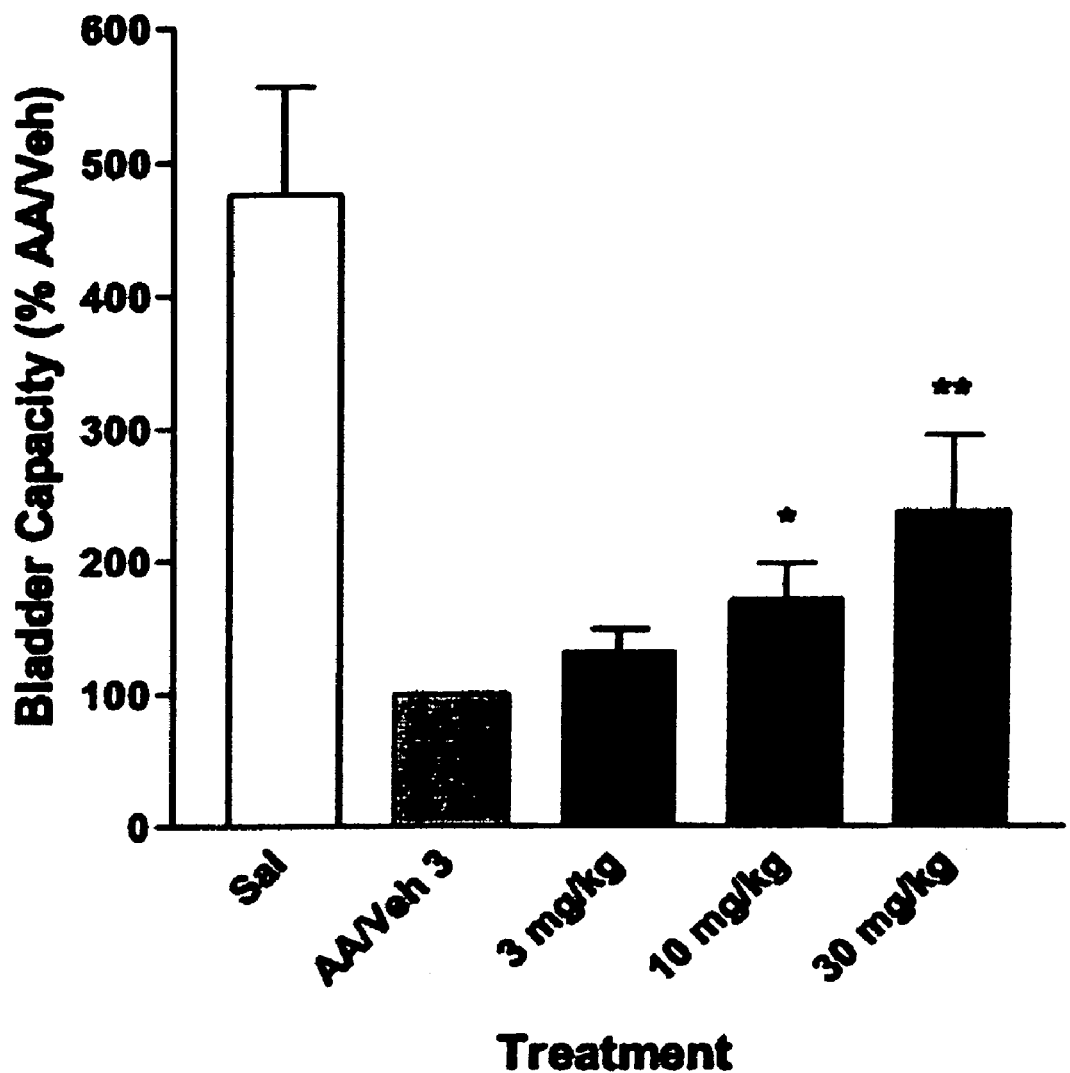
FIG. 1 is a graph of bladder capacity (reported as % Bladder Capacity normalized to the last vehicle treatment measurement of the AA/Veh 3 treatment group) for the indicated treatment regimen in female rats subjected to the dilute acetic acid model described herein (Sal=saline).

The invention relates to a method of treating at least one symptom of a lower urinary tract disorder in a subject in need of treatment wherein the symptom is selected from the group consisting of urinary frequency, urinary urgency, urinary urge incontinence, nocturia and enuresis. In one embodiment, the lower urinary tract disorder can be selected from the group consisting of overactive bladder, interstitial cystitis, prostatitis, prostadynia and benign prostatic hyperplasia. In another embodiment, the lower urinary tract disorder is overactive bladder. In yet another embodiment, the lower urinary tract disorder is interstitial cystitis.

Monoamine Neurotransmitters:

Monoamine neurotransmitters such as noradrenaline (also referred to as norepinephrine), serotonin (5-hydroxytryptamine, 5-HT) and dopamine are known and disturbances in these neurotransmitters have been indicated in many types of disorders, such as depression. These neurotransmitters travel from the terminal of a neuron across a small gap referred to as the synaptic cleft and bind to receptor molecules on the surface of a second neuron. This binding elicits intracellular changes that initiate or activate a response or change in the postsynaptic neuron. Inactivation occurs primarily by transport of the neurotransmitter back into the presynaptic neuron, which is referred to as reuptake. These neurons or neuroendocrine cells can be found both in the Central Nervous System (CNS) and in the Peripheral Nervous System (PNS).

Noradrenaline and Noradrenaline Reuptake Inhibitors:

As used herein, the term NorAdrenaline Reuptake Inhibitor (NARI) refers to an agent (e.g., a molecule, a compound) which can inhibit noradrenaline transporter function. For example, a NARI can inhibit binding of a ligand of a noradrenaline transporter to said transporter and/or inhibit transport (e.g., uptake or reuptake of noradrenaline). As such, inhibition of the noradrenaline transport function in a subject, can result in an increase in the concentration of physiologically active noradrenaline. It is understood that NorAdrenergic Reuptake Inhibitor and NorEpinephrine Reuptake Inhibitor (NERI) are synonymous with NorAdrenaline Reuptake Inhibitor (NARI).

As used herein, noradrenaline transporter refers to naturally occurring noradrenaline transporters (e.g., mammalian noradrenaline transporters (e.g., human (*Homo sapiens*) noradrenaline transporters, murine (e.g., rat, mouse) noradrenaline transporters)) and to proteins having an amino acid sequence which is the same as that of a corresponding naturally occurring noradrenaline transporter (e.g., recombinant proteins). The term includes naturally occurring variants, such as polymorphic or allelic variants and splice variants.

In certain embodiments, the NARI can inhibit the binding of a ligand (e.g., a natural ligand such as noradrenaline, or other ligand such as nisoxetine) to a noradrenaline transporter. In other embodiments, the NARI can bind to a noradrenaline transporter. For example, in a preferred embodiment, the NARI can bind to a noradrenaline transporter, thereby inhibiting binding of a ligand to said transporter and inhibiting transport of said ligand. In another preferred embodiment, the NARI can bind to a noradrenaline transporter, and thereby inhibit transport.

The NARI activity of a compound can be determined employing suitable assays. More specifically, to determine the inhibition constant (Ki) for noradrenaline reuptake, an assay which monitors inhibition of noradrenaline (NA) uptake can be used. For example, radiolabelled noradrenaline, such as [$^3$H]NA and the test compound of interest can be incubated under conditions suitable for uptake with brain tissue or a suitable fraction thereof, for example, a synaptosomal fraction from rat brain tissue (harvested and isolated in accordance with generally accepted techniques), and the amount of uptake of [$^3$H]NA in the tissue or fraction can be determined (e.g., by liquid scintillation spectrometry). $IC_{50}$ values can be calculated by nonlinear regression analysis. The inhibition constants, Ki values, can then be calculated from the $IC_{50}$ values using the Cheng-Prusoff equation:

$$K_i = \frac{IC_{50}}{1 + ([L]/K_d)}$$

wherein [L]=the concentration of free radioligand used in the assay and $K_d$=the equilibrium dissociation constant of the radioligand. To determine the non-specific uptake, incubations can be performed by following the same assay, but in the absence of test compound at 4° C. (i.e., under conditions not suitable for uptake).

In a preferred embodiment, NARI activity is determined using the radioligand uptake assay described above, according to the procedure detailed in Eguchi et al., *Arzneim.-Forschung/Drug Res.*, 47(12): 1337–47 (1997).

Specifically, rats are decapitated and the cortical, hypothalamic, hippocampal and striatal tissues are rapidly dissected. The tissues are homogenized (Potter homogenizer with Teflon pestle) in 10 volumes of ice cold 0.32 mol/L sucrose. The $P_2$ fraction is obtained by centrifugation at 1000×g for 10 minutes and 11500×g for 20 minutes and suspended in Krebs-Ringer phosphate buffer, pH 7.4 (124 mmol/L NaCl, 5 mmol/L KCl, 20 mmol/L $Na_2HPO_4$, 1.2 mmol/L $KH_2PO_4$, 1.3 mmol/L $MgSO_4$, 0.75 mmol/L $CaCl_2$, 10 mmol/L glucose). The [$^3$H]NA uptake assays are performed on the cortical and hypothalamic synaptosomes.

The assay tubes contain radiolabled noradrenaline, [$^3$H] NA, in a volume of 0.2 mL, compounds at 5 or more concentrations in a volume of 0.1 mL, and the oxygenated buffer described above in a volume of 0.5 mL. After 5 minutes preincubation at 37 ° C., uptake is initiated by the addition of the synaptosomal fraction in volume of 0.2 mL. The final concentration of [$^3$H]NA in the incubation mixtures is 0.25 µmol/L. The reaction is stopped after 5 minutes by filtration through Whatman GF/B glass fiber filter under a vacuum with a cell harvester. The filter is rinsed three times with 4 mL of saline and placed in a scintillation vial containing 10 mL of Atomlight (Du Pont/NEN Research Products). Radioactivity is measured by liquid scintillation spectrometry. For determination of non-specific uptake, incubations are performed at 4° C. without the addition of test compounds. $IC_{50}$ values are calculated by nonlinear regression analysis. Inhibitor constants, Ki values, are calculated from the $IC_{50}$ values using the Cheng-Prusoff equation.

NARI compounds suitable for use in the invention have a Ki value for NARI activity of about 500 nmol/L or less, such as about 250 nmol/L or less, for example, about 100 nmol/L or less. It is preferred that the Ki value for NARI activity be about 100 nmol/L or less. It is understood that the exact value of the Ki for a particular compound can vary depending on the assay conditions employed for determination (e.g., radioligand and tissue source). As such, it is preferred that the NARI activity be assessed essentially according to the radioligand binding assay described in Eguchi et al., Arzneim.-Forschung/Drug Res., 47(12): 1337–47 (1997) and discussed in detail above.

In addition, to possessing sufficient NARI activity, it is preferred that the NARI compounds possess one or more characteristics selected from the group consisting of:
  a) the substantial absence of anticholinergic effects;
  b) the selective inhibition of noradrenaline reuptake as compared to inhibition of serotonin reuptake; and
  c) the selective inhibition of noradrenaline reuptake as compared to inhibition of dopamine reuptake.

Selective inhibition of noradrenaline reuptake as compared to inhibition of serotonin or dopamine reuptake can be determined by comparing the Ki values for the respective reuptake inhibitions. The inhibition constants for serotonin and dopamine reuptake can be determined as described above for nordrenaline, but employing the appropriate radioligand and tissue for the activity being assessed (e.g., [3H]5-HT for serotonin, using e.g., hypothalamic or cortical tissue and [$^3$H]DA for dopamine (DA), using e.g., striatal tissue).

A preferred method of determining serotonin reuptake inhibition and dopaminergic reuptake inhibition is described in Eguchi et al., Arzneim.-Forschung/Drug Res., 47(12): 1337–47 (1997). Specifically, rats are decapitated and the cortical, hypothalamic, hippocampal and striatal tissues are rapidly dissected. The tissues are homogenized (Potter homogenizer with Teflon pestle) in 10 volumes of ice cold 0.32 mol/L sucrose. The $P_2$ fraction is obtained by centrifugation at 1000×g for 10 minutes and 11500×g for 20 minutes and suspended in Krebs-Ringer phosphate buffer, pH 7.4 (124 mmol/L NaCl, 5 mmol/L KCl, 20 mmol/L Na2HPO$_4$, 1.2 mmol/L KH$_2$PO$_4$, 1.3 mmol/L MgSO$_4$, 0.75 mmol/L CaCl$_2$, 10 mmol/L glucose). The [$^3$H]5-HT uptake assays are performed on the cortical, hypothalamic and hippocampal synaptosomes, and the [$^3$H]DA uptake assays are performed on striatal synaptosomes.

The assay tubes contain the appropriate radiolabeled ligand (i.e., [$^3$H]5-HT or [$^3$H]DA), in a volume of 0.2 mL, compounds at 5 or more concentrations in a volume of 0.1 mL, and the oxygenated buffer described above in a volume of 0.5 mL. After 5 minutes preincubation at 37° C., uptake is initiated by the addition of the synaptosomal fraction in volume of 0.2 mL. The final concentration of [$^3$H]DA in the striatal incubation mixtures is 0.4 μmol/L. The final concentrations of [$^3$H]5-HT in the cortical, hypothalamic and hippocampal synaptosome incubation mixtures are 0.02 μmol/L, 0.04 μmol/L and 0.08 μmol/L. The reaction is stopped after 5 minutes ([$^3$H]5-HT) or 3 minutes [$^3$H]DA by filtration through Whatman GF/B glass fiber filter under a vacuum with a cell harvester. The filter is rinsed three times with 4 mL of saline and placed in a scintillation vial containing 10 mL of Atomlight (Du Pont/NEN Research Products). Radioactivity is measured by liquid scintillation spectrometry. For determination of non-specific uptake incubations are performed at 4° C. without the addition of test compounds. $IC_{50}$ values are calculated by nonlinear regression analysis. Inhibition constants, Ki values, are calculated from the $IC_{50}$ values using the Cheng-Prusoff equation.

Following determination of the Ki values for inhibition of noradrenaline, serotonin and/or dopamine uptake, the ratio of the activities can be determined. Selective inhibition of noradrenaline reuptake as compared to inhibition of serotonin reuptake and/or dopaminergic reuptake, refers to a compound having a Ki value for inhibition of serotonin (re)uptake and/or dopamine (re)uptake which is about 10 times or more than the Ki for inhibition of noradrenaline (re)uptake. That is, the ratio, Ki inhibition of serotonin (re)uptake/Ki inhibition of noradrenaline (re)uptake, is about 10 or more, such as about 15 or more, about 20 or more, for example, about 30, 40 or 50 or more. Likewise, the ratio, Ki inhibition of dopamine (re)uptake/Ki inhibition noradrenaline (re)uptake, is about 10 or more, such as about 15 or more, about 20 or more, for example, about 30, 40 or 50 or more.

It is preferred that the Ki values for comparison are determined according to the method of Eguchi et al., discussed in detail above. It is most preferred, that the Ki values for NARI activity and inhibition of serotonin reuptake activity, which are compared to determine selective inhibition are determined according to the method of Eguchi et al. using a synaptosomal preparation from rat hypothalamic tissue. Further, it is most preferred, that the Ki values for NARI activity and inhibition of dopamine reuptake activity, which are compared to determine selective inhibition are determined according to the method of Eguchi et al. using a synaptosomal preparation from rat hypothalamic tissue for inhibition of noradrenaline uptake and from rat striatal tissue for inhibition of dopamine uptake.

In another embodiment, the NARI is characterized by the substantial absence of anticholinergic effects. As used herein, substantial absence of anticholinergic effects, refers to a compound which has an $IC_{50}$ value for binding to muscarinic receptors of about 1μmol/L or more. The $IC_{50}$ value for binding to muscarinic receptors can be determined using a suitable assay, such as an assay which determines the ability of a compound to inhibit the binding of suitable radioligand to muscarinic receptors. A preferred assay for determination of the $IC_{50}$ value for binding of a compound to muscarinic receptors is described in Eguchi et al., Arzneim.-Forschung/Drug Res., 47(12): 1337–47 (1997).

Specifically, the binding assays for determination of binding to muscarinic receptors can be performed on tissue isolated from the rat cerebral cortex. The buffer is any suitable buffer, for example, 50 mmol/L Tris-HCl, pH=7.4. The preferred radiolabeled ligand is [$^3$H]QNB (3-quinuclidinyl benzilate) which is present in a final concentration of 0.2 nmol/L. The test compound is added at various concentrations and the resulting mixtures are incubated for 60 minutes at 37° C. The reaction is terminated by rapid vacuum filtration onto glass fiber filter. Radioactivity trapped on the filter is measured by scintillation spectrometry. Non-specific binding is determined using 100 μmol/L atropine. $IC_{50}$ values can be calculated by nonlinear regression analysis.

In a particular embodiment, the NARI compound can be selected from venlafaxine, duloxetine, buproprion, milnacipran, reboxetine, lefepramine, desipramine, nortriptyline, tomoxetine, maprotiline, oxaprotiline, levoprotiline, viloxazine and atomoxetine.

In a preferred embodiment, the NARI compound can be selected from reboxetine, lefepramine, desipramine, nortriptyline, tomoxetine, maprotiline, oxaprotiline, levoprotiline, viloxazine and atomoxetine.

Serotonin and 5-HT$_3$ Receptor Antagonists:

The neurotransmitter serotonin was first discovered in 1948 and has subsequently been the subject of substantial scientific research. Serotonin, also referred to as 5-hydroxytryptamine (5-HT), acts both centrally and peripherally on discrete 5-HT receptors. Currently, fourteen subtypes of serotonin receptors are recognized and delineated into seven families, 5-HT$_1$ through 5-HT$_7$. These subtypes share sequence homology and display some similarities in their specificity for particular ligands. A review of the nomenclature and classification of the 5-HT receptors can be found in Neuropharm., 33: 261–273 (1994) and Pharm. Rev., 46:157–203 (1994).

Recent animal studies have suggested that targeting specific subtypes of 5-HT receptors could offer additional treatments for lower urinary tract dysfunctions. For example, among the various subtypes of 5-HT receptors, 5-HT$_2$ and 5-HT$_3$ receptors mediate excitatory effects on sympathetic and somatic reflexes to increase outlet resistance. Moreover, 5-HT$_{2C}$ and 5-HT$_3$ receptors have also been shown to be involved in inhibition of the micturition reflex (Downie, J. W. (1999) Pharmacological manipulation of central micturition circuitry. Curr. Opin. SPNS Inves. Drugs 1:23). In fact, 5-HT$_3$ receptor inhibition has been shown to diminish 5-HT mediated contractions in rabbit detrusor (Khan, M. A. et al. (2000) Doxazosin modifies serotonin-mediated rabbit urinary bladder contraction. Potential clinical relevance. Urol. Res. 28:116).

As used herein, 5-HT$_3$ receptor refers to naturally occurring 5-HT$_3$ receptors (e.g., mammalian 5-HT$_3$ receptors (e.g., human (Homo sapiens) 5-HT$_3$ receptors, murine (e.g., rat, mouse) 5-HT$_3$ receptors)) and to proteins having an amino acid sequence which is the same as that of a corresponding naturally occurring 5-HT$_3$ receptor (e.g., recombinant proteins). The term includes naturally occurring variants, such as polymorphic or allelic variants and splice variants.

As used herein, the term 5-HT$_3$ receptor antagonist refers to an agent (e.g., a molecule, a compound) which can inhibit 5-HT$_3$ receptor function. For example, a 5-HT$_3$ receptor antagonist can inhibit binding of a ligand of a 5-HT$_3$ receptor to said receptor and/or inhibit a 5-HT$_3$ receptor-mediated response (e.g., reduce the ability of 5-HT$_3$ to evoke the von Bezold-Jarisch reflex).

In certain embodiments, the 5-HT$_3$ receptor antagonist can inhibit binding of a ligand (e.g., a natural ligand, such as serotonin (5-HT$_3$), or other ligand such as GR65630) to a 5-HT$_3$ receptor. In certain embodiments, the 5-HT$_3$ receptor antagonist can bind to a 5-HT$_3$ receptor. For example, in a preferred embodiment, the 5-HT$_3$ receptor antagonist can bind to a 5-HT$_3$ receptor, thereby inhibiting the binding of a ligand to said receptor and a 5-HT$_3$ receptor-mediated response to ligand binding. In another preferred embodiment, the 5-HT$_3$ receptor antagonist can bind to a 5-HT$_3$ receptor, and thereby inhibit a 5-HT$_3$ receptor-mediated response.

5-HT$_3$ receptor antagonists can be identified and activity assessed by any suitable method, for example, by a method which assesses the ability of a compound to inhibit radioligand binding to 5-HT$_3$ receptor (see, for example, Eguchi et al., Arzneim.-Forschung/Drug Res., 47(12): 1337–47 (1997) and G. Kilpatrick et al., Nature, 330: 746–748 (1987)) and/or by their effect on the 5-HT$_3$-induced von Bezold-Jarisch (B-J) reflex in the cat or rat (following the general methods described by Butler et al., Br. J. Pharmacol., 94: 397–412 (1988) and Ito et al., J. Pharmacol. Exp. Ther., 280(1): 67–72 (1997), respectively).

In a preferred embodiment, 5-HT$_3$ receptor antagonist activity of a compound can be determined according to the method described in Eguchi et al., Arzneim.-Forschung/Drug Res., 47(12): 1337–47 (1997). Specifically, the binding assays for determination of binding to the 5-HT$_3$ receptor can be performed on N1E-115 mouse neuroblastoma cells (American Type Culture Collection (ATCC) Accession No. CRL-2263) in 20 mmol/L HEPES buffer (pH=7.4) containing 150 mmol/L NaCl, 0.35 mmol/L of radiolabeled ligand ([$^3$H]GR65630) and the test compound at 6 or more concentrations at 25° C. for 60 minutes. The reaction is terminated by rapid vacuum filtration onto glass fiber filter. Radioactivity trapped on the filter is measured by scintillation spectrometry. Non-specific binding is determined using 1 μmol/L of MDL-7222 (endo-8-methyl-8-azabicyclo [3.2.1]oct-3-yl-3,5-dichlorobenzoate. IC$_{50}$ values are calculated by nonlinear regression analysis. The affinity constants, Ki values, are calculated from the IC$_{50}$ values using the Cheng-Prusoff equation.

Compounds having 5-HT$_3$ receptor antagonist activity which are suitable for use in the invention have an affinity for 5-HT$_3$ receptor (Ki) of not more than about 250 times the Ki of ondansetron for 5-HT$_3$ receptor. This relative activity to ondansetron (Ki of test agent for 5-HT$_3$ receptor/Ki of ondansetron for 5-HT$_3$ receptor), can be determined by assaying the compound of interest and ondansetron using a suitable assay under controlled conditions, for example, conditions which differ primarily in the agent being tested. It is preferred that the relative activity of the 5-HT$_3$ receptor antagonist activity be not more than about 200 times that of ondansetron, for example, not more than about 150 times that of ondansetron, such as not more than about 100 times that of ondansetron, for example, not more than about 50 times that of ondansetron. In a particularly preferred embodiment, the compound having 5-HT$_3$ receptor antagonist activity has a relative activity to ondansetron of not more than about 10.

In certain embodiments, the 5-HT$_3$ receptor antagonist can be selected from indisetron, YM-114 ((R)-2,3-dihydro-1-[(4,5,6,7-tetrahydro-1H-benzimidazol-5-yl-)carbonyl]-1H-indole), granisetron, talipexole, azasetron, bemesetron, tropisetron, ramosetron, ondansetron, palonosetron, lerisetron, alosetron, N-3389, zacopride, cilansetron, E-3620 ([3(S)-endo]-4-amino-5-chloro-N-(8-methyl-8-azabicyclo [3.2.1-]oct-3-yl-2[(1-methyl-2-butynyl)oxy]benzamide), lintopride, KAE-393, itasetron, zatosetron, dolasetron, (±)-zacopride, (±)-renzapride, (−)-YM-060, DAU-6236, BIMU-8 and GK-128 ([2-[2-methylimidazol-1-yl)methyl]-benzo[f]thiochromen-1-one monohydrochloride hemihydrate]).

In preferred embodiments, the 5-HT$_3$ receptor antagonist can be selected from indisetron, granisetron, azasetron, bemesetron, tropisetron, ramosetron, ondansetron, palonosetron, lerisetron, alosetron, cilansetron, itasetron, zatosetron, and dolasetron.

As used herein, lower urinary tract refers to all parts of the urinary tract except the kidneys.

As used herein, lower urinary tract disorder refers to any disorder involving the lower urinary tract, including but not limited to overactive bladder, interstitial cystitis, prostatitis, prostadynia and benign prostatic hyperplasia.

As used herein, bladder disorder refers to any condition involving the urinary bladder.

As used herein, overactive bladder refers to a chronic condition resulting from overactivity of the detrusor muscle, wherein the bladder initiates contraction too early while filling with urine, manifesting with one or more symptoms of urinary frequency, urinary urgency, urinary urge incontinence, nocturia or enuresis. Overactive bladder can be neurogenic or non-neurogenic.

Neurogenic overactive bladder (or neurogenic bladder) is a type of overactive bladder which occurs as a result of detrusor muscle overactivity referred to as detrusor hyperreflexia, secondary to neurologic disorders.

Non-neurogenic overactive bladder occurs as a result of detrusor muscle overactivity referred to as detrusor muscle instability. Detrusor muscle instability can arise from non-neurological abnormalities, such as bladder stones, muscle disease, urinary tract infection or drug side effects or can be idiopathic.

Interstitial cystitis is used herein in its conventional sense to refer to a disorder associated with symptoms that can include irritative voiding symptoms, urinary frequency, urgency, nocturia, suprapubic pain and/or pelvic pain related to and relieved by voiding.

As used herein, urinary frequency refers to urinating more frequently than the patient desires. As there is considerable interpersonal variation in the number of times in a day that an individual would normally expect to urinate, "more frequently than the patient desires" is further defined as a greater number of times per day than that patient's historical baseline. "Historical baseline" is further defined as the median number of times the patient urinated per day during a normal or desirable time period.

As used herein, urinary urgency refers to sudden strong urges to urinate with little or no chance to postpone the urination.

As used herein, urinary urge incontinence (also referred to as urge incontinence) refers to the involuntary loss of urine associated with urinary urgency.

As used herein, nocturia refers to being awakened from sleep to urinate more frequently than the patient desires.

As used herein, enuresis refers to involuntary voiding of urine which can be complete or incomplete. Nocturnal enuresis refers to enuresis which occurs during sleep. Diurnal enuresis refers to enuresis which occurs while awake.

As used herein, stress incontinence or urinary stress incontinence refers to a medical condition in which urine leaks when a person coughs, sneezes, laughs, exercises, lifts heavy objects, or does anything that puts pressure on the bladder.

As used herein, prostatitis refers to any type of disorder associated with inflammation of the prostate, including chronic and acute bacterial prostatitis and chronic non-bacterial prostatitis, and which is usually associated with symptoms of urinary frequency and/or urinary urgency.

Acute and chronic bacterial prostatitis are used herein in the conventional sense to refer to a disorder characterized by inflammation of the prostate and bacterial infection of the prostate gland, usually associated with symptoms of pain, urinary frequency and/or urinary urgency. Chronic bacterial prostatitis is distinguished from acute bacterial prostatitis based on the recurrent nature of the disorder. Chronic non-bacterial prostatitis is used herein in its conventional sense to refer to a disorder characterized by inflammation of the prostate which is of unknown etiology accompanied by the presence of an excessive amount of inflammatory cells in prostatic secretions not currently associated with bacterial infection of the prostate gland, and usually associated with symptoms of pain, urinary frequency and/or urinary urgency.

Prostadynia is a disorder which mimics the symptoms of prostatitis absent inflammation of the prostate, bacterial infection of the prostate and elevated levels inflammatory cells in prostatic secretions. Prostadynia can be associated with symptoms of pain, urinary frequency and/or urinary urgency.

Benign prostatic hyperplasia is used herein in its conventional sense to refer to a disorder associated with benign enlargement of the prostate gland which can be associated with urinary frequency, urinary urgency, urge incontinence, nocturia, and/or reduced urinary force and speed of flow.

The invention relates to a method of treating at least one symptom of a lower urinary tract disorder in a subject in need of treatment wherein the symptom is selected from the group consisting of urinary frequency, urinary urgency, urinary urge incontinence, nocturia and enuresis. The method comprises administering to a subject in need of treatment a therapeutically effective amount of a compound that has 5-HT$_3$ receptor antagonist activity and NorAdrenaline Reuptake Inhibitor (NARI) activity.

In a particular embodiment, the compounds having 5-HT$_3$ receptor antagonist activity and NARI activity are thieno[2,3-d]pyrimidine derivatives such as those described in U.S. Pat. No. 4,695,568, the entire content of which is incorporated herein by reference.

In a specific embodiment, the compounds having 5-HT$_3$ receptor antagonist activity and NARI activity are represented by Formula I:

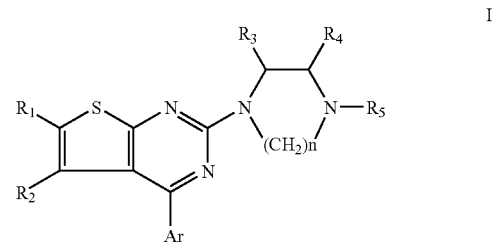

wherein, $R_1$ and $R_2$ independently represent hydrogen, halogen or a $C_1$–$C_6$ alkyl group; or $R_1$ and $R_2$ together with the carbon atoms to which they are attached form a cycloalkylene group having 5 to 6 carbon atoms;

$R_3$ and $R_4$ independently represent hydrogen or a $C_1$–$C_6$ alkyl group;

$R_5$ is hydrogen, $C_1$–$C_6$ alkyl,

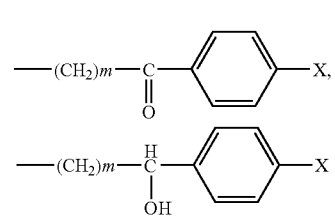

or —C(O)—NH—R$_6$, wherein m is an integer from about 1 to about 3, X is halogen and R$_6$ is a $C_1$–$C_6$ alkyl group;

Ar is a substituted or unsubstituted phenyl, 2-thienyl or 3-thienyl group; and n is 2 or 3; or a pharmaceutically acceptable salt thereof.

Substituted phenyl, 2-thienyl or 3-thienyl group refers to a phenyl, 2-thienyl or 3-thienyl group in which at least one of the hydrogen atoms available for substitution has been replaced with a group other than hydrogen (i.e., a substituent group). Multiple substituent groups can be present on the phenyl, 2-thienyl or 3-thienyl ring. When multiple substituents are present, the substituents can be the same or different and substitution can be at any of the substitutable sites on the ring. Substituent groups can be, for example, a halogen atom (fluorine, chlorine, bromine or iodine); an alkyl group, for example, a $C_1$–$C_6$ alkyl group such as a methyl, ethyl, propyl, butyl, pentyl or hexyl group; an alkoxy group, for example, a $C_1$–$C_6$ alkoxy group such as methoxy, ethoxy, propoxy, butoxy; a hydroxy group; a nitro group; an amino group; a cyano group; or an alkyl substituted amino group such as methylamino, ethylamino, dimethylamino or diethylamino group.

$C_1$–$C_6$ alkyl group refers to a straight-chain or branched alkyl group having from one to six carbon atoms. For example, the $C_1$–$C_6$ alkyl group can be a strain-chain alkyl such as methyl, ethyl, propyl, etc. Alternatively, the alkyl group can be branched for example, an isopropyl or t-butyl group.

Halogen refers to fluorine, chlorine, bromine or iodine.

In a particular embodiment, the compounds having 5-$HT_3$ receptor antagonist activity and NARI activity are represented by Formula I, wherein $R_1$ is a $C_1$–$C_6$ alkyl group and Ar is a substituted phenyl. In this embodiment, it is preferred that the phenyl group is substituted with a halogen.

In a particularly preferred embodiment, the compounds having 5-$HT_3$ receptor antagonist activity and NARI activity are represented by Formula I, wherein n is 2, $R_1$ is a $C_1$–$C_6$ alkyl group and Ar is a substituted phenyl. Preferably, the phenyl group is substituted with a halogen and the alkyl group of $R_1$ is a methyl group.

In yet another embodiment, the compounds having 5-$HT_3$ receptor antagonist activity and NARI activity are represented by Formula I, wherein $R_1$ is a $C_1$–$C_6$ alkyl group or a halogen and Ar is an unsubstituted phenyl. Further, when $R_1$ is an alkyl group and Ar is an unsubstituted phenyl, $R_2$ can also be a hydrogen or a $C_1$–$C_6$ alkyl group.

In a particularly preferred embodiment, the compounds having 5-$HT_3$ receptor antagonist activity and NARI activity are represented by Formula I, wherein n is 2, $R_1$ is a $C_1$–$C_6$ alkyl group and Ar is an unsubstituted phenyl. In a specific embodiment, wherein n is 2, $R_1$ is a $C_1$–$C_6$ alkyl group and Ar is an unsubstituted phenyl, $R_2$ can be hydrogen or a $C_1$–$C_6$ alkyl group.

In a particularly preferred embodiment, the compound having 5-$HT_3$ receptor antagonist activity and NARI activity is represented by structural Formula II:

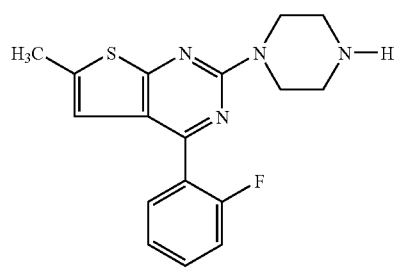

II or a pharmaceutically acceptable salt thereof. This compound is commonly referred to in the art as MCI-225, also referred to as DDP-225. The chemical name of the structure set forth in the formula is: 4-(2-fluorophenyl)-6-methyl-2-(1-piperazinyl)thieno[2,3-d]pyrimidine.

In one embodiment, the lower urinary tract disorder can be selected from the group consisting of overactive bladder, interstitial cystitis, prostatitis, prostadynia and benign prostatic hyperplasia.

In another embodiment, the lower urinary tract disorder is overactive bladder.

In yet another embodiment, the lower urinary tract disorder is interstitial cystitis.

In another embodiment, the method further comprises administering a therapeutically effective amount of an (i.e., one or more) additional therapeutic agent.

Compounds having 5-$HT_3$ receptor antagonist activity and NARI activity, such as the compounds represented by structural Formulas I and II are useful for treating at least one symptom of a lower urinary tract disorder selected from the group consisting of urinary frequency, urinary urgency, urinary urge incontinence, nocturia and enuresis, by virtue of the dual therapeutic modes of action which they can exhibit. That is, the unique ability to modulate the function of both the 5-$HT_3$ receptor and the noradrenaline reuptake mechanism can provide an enhanced treatment regimen for the subject undergoing treatment. For example, the ability to treat at least one symptom of a lower urinary tract disorder by modulating both peripheral and central effects can provide enhanced treatment.

In a preferred embodiment, compounds having 5-$HT_3$ receptor antagonist activity and NARI activity, such as the compounds of Formula I and II possess one or more characteristics selected from the group consisting of:
   a) the substantial absence of anticholinergic effects;
   b) the selective inhibition of noradrenaline reuptake as compared to inhibition of serotonin reuptake; and
   c) the selective inhibition of noradrenaline reuptake as compared to inhibition of dopamine reuptake.

For example, the specific compound MCI-225 has been shown to be a selective NARI and a 5-$HT_3$ receptor antagonist with substantially no anticholinergic activity. Eguchi et al., *Arzneim.-Forschung/Drug Res.*, 47(12): 1337–47 (1997), reported inhibition constants for MCI-225 for the uptake the [$^3$H]monoamine neurotransmitters noradrenaline, serotonin and dopamine in various rat brain tissues. More specifically, MCI-225 inhibited the uptake of [$^3$H]NA and [$^3$H]5-HT by synaptosomes from rat hypothalamic tissue with inhibition constants of Ki=35.0 nmol/L and Ki=491 nmol/L, respectively. In addition, MCI-225 inhibited the uptake of [$^3$H]NA and [$^3$H]5-HT by synaptosomes from rat cortical tissue with inhibition constants of Ki=0.696 nmol/L and Ki=1070 nmol/L, respectively. MCI-225 was also reported to inhibit the uptake of serotonin by synaptosomes from rat hippocampal tissue with an inhibition constant of Ki=244 nmol/L. Further, the MCI-225 inhibition constant for the uptake of [$^3$H]DA by synaptosomes from rat striatal tissue was reported as Ki=14,800. MCI-225 did not inhibit Monoamine Oxidase-A (MAO-A) and Monoamine Oxidase-B (MAO-B) activities.

With regard to 5-$HT_3$ receptor antagonist activity, Eguchi et al. reported that MCI-225 showed high affinity for the 5-$HT_3$ receptor (Ki less than 100 nmol/L) in comparison to the other receptors tested. In addition, MCI-225 showed affinity for the 5-$HT_3$ receptor similar to that reported for ondansetron in the same radioligand binding assay. Briefly, the inhibition of radiolabeled ligand binding by MCI-225, using a suitable radioligand and tissue combination for the receptor of interest was determined. The receptors tested included, $\alpha_1$, $\alpha_2$, $\beta_1$, $\beta_2$, 5-HT$_1$, 5-HT$_{1A}$, 5-HT$_{1c}$, 5-HT$_2$, 5-HT$_3$, 5-HT$_4$, 5-HT$_6$, 5-HT$_7$, D$_1$, D$_2$, Muscarinic, M$_1$, M$_2$, M$_3$, Nicotonic, H$_1$, H$_2$, GABA-A, GABA-B, BZP, Opiate non-selective, Opiate κ, Opiate μ, Opiate δ, CRF (Corticotropin Releasing Factor) and glucocorticoid. The IC$_{50}$ values determined for MCI-225, for these additional receptors were all greater than 1 μmol/L.

The invention further relates to a method of treating at least one symptom of a lower urinary tract disorder in a subject in need of treatment wherein the symptom is selected from the group consisting of urinary frequency, urinary urgency, urinary urge incontinence, nocturia and enuresis, comprising coadministering to said subject a therapeutically effective amount of a 5-HT$_3$ receptor antagonist and a therapeutically effective amount of a NARI.

The invention further relates to a method of treating at least one symptom of a lower urinary tract disorder in a subject in need of treatment wherein the symptom is selected from the group consisting of urinary frequency, urinary urgency, urinary urge incontinence, nocturia and enuresis comprising coadministering to said subject a first amount of a 5-HT$_3$ receptor antagonist and a second amount of a NARI, wherein the first and second amounts together comprise a therapeutically effective amount.

In one embodiment, the lower urinary tract disorder can be selected from the group consisting of overactive bladder, interstitial cystitis, prostatitis, prostadynia and benign prostatic hyperplasia.

In another embodiment, the lower urinary tract disorder is overactive bladder.

In yet another embodiment, the lower urinary tract disorder is interstitial cystitis.

In another embodiment, the coadministration methods further comprise administering a therapeutically effective amount of an (i.e., one or more) additional therapeutic agent.

In certain embodiments of the coadministration method, the 5-HT$_3$ receptor antagonist can be selected from indisetron, YM-114 ((R)-2,3-dihydro-1-[(4,5,6,7-tetrahydro-1H-benzimidazol-5-yl-)carbonyl]-1H-indole), granisetron, talipexole, azasetron, bemesetron, tropisetron, ramosetron, ondansetron, palonosetron, lerisetron, alosetron, N-3389, zacopride, cilansetron, E-3620 ([3(S)-endo]-4-amino-5-chloro-N-(8-methyl-8-azabicyclo[3.2.1-]oct-3-yl-2[(1-methyl-2-butynyl)oxy]benzamide), lintopride, KAE-393, itasetron, zatosetron, dolasetron, (±)-zacopride, (±)-renzapride, (−)-YM-060, DAU-6236, BIMU-8 and GK-128 ([2-[2-methylimidazol-1-yl)methyl]-benzo[ƒ]thiochromen-1-one monohydrochloride hemihydrate]).

In preferred embodiments, the 5-HT$_3$ receptor antagonist can be selected from indisetron, granisetron, azasetron, bemesetron, tropisetron, ramosetron, ondansetron, palonosetron, lerisetron, alosetron, cilansetron, itasetron, zatosetron, and dolasetron.

In certain embodiments, the NARI compound can be selected from venlafaxine, duloxetine, buproprion, milnacipran, reboxetine, lefepramine, desipramine, nortriptyline, tomoxetine, maprotiline, oxaprotiline, levoprotiline, viloxazine and atomoxetine.

In a preferred embodiment, the NARI compound can be selected from reboxetine, lefepramine, desipramine, nortriptyline, tomoxetine, maprotiline, oxaprotiline, levoprotiline, viloxazine and atomoxetine.

In a preferred embodiment, the NARI compound possesses one or more characteristics selected from the group consisting of:

a) the substantial absence of anticholinergic effects;
b) the selective inhibition of noradrenaline reuptake as compared to inhibition of serotonin reuptake; and
c) the selective inhibition of noradrenaline reuptake as compared to inhibition of dopamine reuptake.

The invention further relates to pharmaceutical compositions useful for the treatment of at least one symptom of a lower urinary tract disorder in a subject in need of treatment wherein the symptom is selected from the group consisting of urinary frequency, urinary urgency, urinary urge incontinence, nocturia and enuresis. The pharmaceutical composition comprises a first amount of a 5-HT$_3$ receptor antagonist compound and a second amount of a NARI compound. The pharmaceutical compositions of the present invention can optionally contain a pharmaceutically acceptable carrier. The 5-HT$_3$ receptor antagonist and the NARI can each be present in the pharmaceutical composition in a therapeutically effective amount. In another aspect, said first and second amounts can together comprise a therapeutically effective amount.

In one embodiment, the lower urinary tract disorder can be selected from the group consisting of overactive bladder, interstitial cystitis, prostatitis, prostadynia and benign prostatic hyperplasia.

In another embodiment, the lower urinary tract disorder is overactive bladder.

In yet another embodiment, the lower urinary tract disorder is interstitial cystitis.

In a further embodiment, the pharmaceutical composition further comprises an (i.e., one or more) additional therapeutic agent.

An additional therapeutic agent suitable for use in the methods and pharmaceutical compositions described herein, can be, but is not limited to, for example: an antimuscarinic (e.g., oxybutynin, DITROPAN®, tolterodine, flavoxate, propiverine, trospium); a muscosal surface protectant (e.g., ELMIRON®); an antihistamine (e.g., hydroxyzine hydrochloride or pamoate); an anticonvulsant (e.g., NEURONTIN® and KLONOPIN®); a muscle relaxant (e.g., VALIUM®); a bladder antispasmodic (e.g., URIMAX®); a tricyclic antidepressant (e.g., imipramine); a nitric oxide donor (e.g., nitroprusside), a β$_3$-adrenergic receptor agonist, a bradykinin receptor antagonist, a neurokinin receptor antagonist, a sodium channel modulator, such as TTX-R sodium channel modulator and/or activity dependent sodium channel modulator and a Cav2.2 subunit calcium channel modulator. Generally, the additional therapeutic agent will be one that is useful for treating the disorder of interest. Preferably, the additional therapeutic agent does not diminish the effects of the primary agent(s) and/or potentiates the effect of the primary agent(s).

Use of an additional therapeutic agent in combination with the primary agent(s) (i.e., a compound having 5-HT$_3$ receptor antagonist activity and NARI activity or a combination of a first compound having 5-HT$_3$ receptor antagonist activity and a second compound having NARI activity) can result in less of any of the primary agent(s) and/or less of the additional agent being needed to achieve therapeutic efficacy. In some instances, use of less of an agent can be advantageous in that it provides a reduction in undesirable side effects.

By the term "antimuscarinic agent" as used herein is intended any muscarinic acetylcholine receptor antagonist. Unless otherwise indicated, the terms "anticholinergic agent," "antinicotinic agent," and "antimuscarinic agent" are intended to include anticholinergic, antinicotinic, and antimuscarinic agents as disclosed further herein, as well as acids, salts, esters, amides, prodrugs, active metabolites, and other derivatives thereof. Further, it is understood that any salts, esters, amides, prodrugs, active metabolites or other derivatives are pharmaceutically acceptable as well as pharmacologically active.

More specifically, oxybutynin, also known as 4-diethylaminio-2-butynyl phenylcyclohexyglycolate is a preferred antimuscarinic agent. It has the following structure:

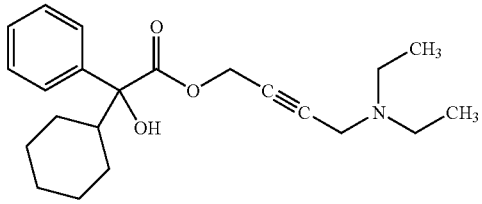

Ditropan® (oxybutynin chloride) is the d,l racemic mixture of the above compound, which is known to exert antispasmodic effect on smooth muscle and inhibit the muscarinic action of acetylcholine on smooth muscle. Metabolites and isomers of oxybutynin have also been shown to have activity useful according to the present invention. Examples include, but are not limited to N-desethyl-oxybutynin and S-oxybutynin (see, e.g., U.S. Pat. Nos. 5,736,577 and 5,532,278).

Additional compounds that have been identified as antimuscarinic agents and are useful in the present invention include, but are not limited to:

a. Darifenacin (Daryon®) or acids, salts, enantiomers, analogs, esters, amides, prodrugs, active metabolites, and derivatives thereof;
b. Solifenacin or acids, salts, enantiomers, analogs, esters, amides, prodrugs, active metabolites, and derivatives thereof;
c. YM-905 (solifenacin succinate) or acids, salts, enantiomers, analogs, esters, amides, prodrugs, active metabolites, and derivatives thereof;
d. Solifenacin monohydrochloride or acids, salts, enantiomers, analogs, esters, amides, prodrugs, active metabolites, and derivatives thereof;
e. Tolterodine (Detrol®) or acids, salts, enantiomers, analogs, esters, amides, prodrugs, active metabolites, and derivatives thereof;
f. Propiverine (Detrunorm®) or acids, salts, enantiomers, analogs, esters, amides, prodrugs, active metabolites, and derivatives thereof;
g. Propantheline bromide (Pro-Banthine®) or acids, salts, enantiomers, analogs, esters, amides, prodrugs, active metabolites, and derivatives thereof;
h. Hyoscyamine sulfate (Levsin®, Cystospaz®) or acids, salts, enantiomers, analogs, esters, amides, prodrugs, active metabolites, and derivatives thereof;
i. Dicyclomine hydrochloride (Bentyl®) or acids, salts, enantiomers, a nalogs, esters, amides, prodrugs, active metabolites, and derivatives thereof;
j. Flavoxate hydrochloride (Urispas®) or acids, salts, enantiomers, analogs, esters, amides, prodrugs, active metabolites, and derivatives thereof;
k. d,l (racemic) 4-diethylamino-2-butynyl phenylcyclohexylglycolate or acids, salts, enantiomers, analogs, esters, amides, prodrugs, active metabolites, and derivatives thereof;
l. (R)-N,N-diisopropyl-3-(2-hydroxy-5-methylphenyl)-3-phenylpropanamine L-hydrogen tartrate or acids, salts, enantiomers, analogs, esters, amides, prodrugs, active metabolites, and derivatives thereof;
m. (+)-(1S,3'R)-quinuclidin-3'-yl-1-phenyl-1,2,3,4-tetrahydro-isoquinoline-2-carboxylate monosuccinate or acids, salts, enantiomers, analogs, esters, amides, prodrugs, active metabolites, and derivatives thereof;
n. alpha(+)-4-(Dimethylamino)-3-methyl-1,2-diphenyl-2-butanol proprionate or acids, salts, enantiomers, analogs, esters, amides, prodrugs, active metabolites, and derivatives thereof;
o. 1-methyl-4-piperidyl diphenylpropoxyacetate or acids, salts, enantiomers, analogs, esters, amides, prodrugs, active metabolites, and derivatives thereof;
p. 3-hydroxyspiro[1H,5H-nortropane-8,1'-pyrrolidinium benzilate or acids, salts, enantiomers, analogs, esters, amides, prodrugs, active metabolites, and derivatives thereof;
q. 4 amino-piperidine containing compounds as disclosed in Diouf et al. (2002) Bioorg. Med. Chem. Lett. 12: 2535–9;
r. pirenzipine or acids, salts, enantiomers, analogs, esters, amides, prodrugs, active metabolites, and derivatives thereof;
s. methoctramine or acids, salts, enantiomers, analogs, esters, amides, prodrugs, active metabolites, and derivatives thereof;
t. 4-diphenylacetoxy-N-methyl piperidine methiodide;
u. tropicamide or acids, salts, enantiomers, analogs, esters, amides, prodrugs, active metabolites, and derivatives thereof;
v. (2R)-N-[1-(6-aminopyridin-2-ylmethyl)piperidin-4-yl]-2-[(1R)-3,3-difluorocyclopentyl]-2-hydroxy-2-phenylacetamide or acids, salts, enantiomers, analogs, esters, amides, prodrugs, active metabolites, and derivatives thereof;
w. PNU-200577 ((R)-N,N-diisopropyl-3-(2-hydroxy-5-hydroxymethylphenyl)-3-phenylpropanamine) or acids, salts, enantiomers, analogs, esters, amides, prodrugs, active metabolites, and derivatives thereof;
x. KRP-197 (4-(2-methylimidazolyl)-2,2-diphenylbutyramide) or acids, salts, enantiomers, analogs, esters, amides, prodrugs, active metabolites, and derivatives thereof;
y. Fesoterodine or acids, salts, enantiomers, analogs, esters, amides, prodrugs, active metabolites, and derivatives thereof; and
z. SPM 7605 (the active metabolite of Fesoterodine), or acids, salts, enantiomers, analogs, esters, amides, prodrugs, active metabolites, and derivatives thereof.

The identification of further compounds that have antimuscarinic activity and would therefore be useful in the present invention can be determined by performing muscarinic receptor binding specificity studies as described by Nilvebrant (2002) Pharmacol. Toxicol. 90: 260–7 or cystometry studies as described by Modiri et al. (2002) Urology 59: 963–8.

The term "$\beta_3$ adrenergic receptor agonist" is used in its conventional sense to refer to a compound that binds to and agonizes $\beta_3$ adrenergic receptors. Unless otherwise indicated, the term $\beta_3$ adrenergic agonist" is intended to include $\beta_3$ adrenergic agonist agents as disclosed further herein, as well as acids, salts, esters, amides, prodrugs, active metabolites, and other derivatives thereof. Further, it is understood that any salts, esters, amides, prodrugs, active metabolites or other derivatives are pharmaceutically acceptable as well as pharmacologically active. Compounds that have been identified as $\beta_3$ adrenergic agonist agents and are useful in the present invention include, but are not limited to:

a. TT-138 and phenylethanolamine compounds as disclosed in U.S. Pat. No. 6,069,176, PCT Publication No. WO 97/15549 and available from Mitsubishi Pharma Corp., or acids, salts, esters, amides, prodrugs, active metabolites, and other derivatives thereof;

b. FR-149174 and propanolamine derivatives as disclosed in U.S. Pat. Nos. 6,495,546 and 6,391,915 and available from Fujisawa Pharmaceutical Co., or acids, salts, esters, amides, prodrugs, active metabolites, and other derivatives thereof;

c. KUC-7483, available from Kissei Pharmaceutical Co., or acids, salts, esters, amides, prodrugs, active metabolites, and other derivatives thereof, d. 4'-hydroxynorephedrine derivatives such as 2-2-chloro-4-(2-((1S,2R)-2-hydroxy-2-(4-hydroxyphenyl)-1-methylethylamino)ethyl)-phenoxy acetic acid as disclosed in Tanaka et al. (2003) *J. Med. Chem.* 46: 105–12 or acids, salts, esters, amides, prodrugs, active metabolites, and other derivatives thereof;

e. 2-amino-1-phenylethanol compounds, such as BRL35135 ((R*R*)-(.+−.)-[4-[2-[2-(3-chlorophenyl)-2-ydroxyethylamino]propyl]phenoxy]acetic acid methyl ester hydrobromide salt as disclosed in Japanese Patent Publication No. 26744 of 1988 and European Patent Publication No. 23385), and SR58611A ((RS)-N-(7-ethoxycarbonylmethoxy-1,2,3,4-tetrahydronaphth-2-yl)-2-(3-chlorophenyl)-2-hydroxyethanamine hydrochloride as disclosed in Japanese Laid-open Patent Publication No. 66152 of 1989 and European Laid-open Patent Publication No. 255415) or acids, salts, esters, amides, prodrugs, active metabolites, and other derivatives thereof;

f. GS 332 (Sodium (2R)-[3-[3-[2-(3Chlorophenyl)-2-hydroxyethylamino]cyclohexyl]phenoxy]acetate) as disclosed in Iizuka et al. (1998) *J. Smooth Muscle Res.* 34: 139–49 or acids, salts, esters, amides, prodrugs, active metabolites, and other derivatives thereof;

g. BRL-37,344 (4-[-[(2-hydroxy-(3-chlorophenyl)ethyl)-amino]propyl]phenoxyacetate) as disclosed in Tsujii et al. (1998) *Physiol. Behav.* 63: 723–8 and available from GlaxoSmithKline or acids, salts, esters, amides, prodrugs, active metabolites, and other derivatives thereof;

h. BRL-26830A as disclosed in Takahashi et al. (1992) *Jpn Circ. J.* 56: 936–42 and available from GlaxoSmithKline or acids, salts, esters, amides, prodrugs, active metabolites, and other derivatives thereof;

i. CGP 12177 (4-[3-t-butylamino-2-hydroxypropoxy]benzimidazol-2-one) (a ½ adrenergic antagonist reported to act as an agonist for the 3 adrenergic receptor) as described in Tavernier et al. (1992) *J. Pharmacol. Exp. Ther.* 263: 1083–90 and available from Ciba-Geigy or acids, salts, esters, amides, prodrugs, active metabolites, and other derivatives thereof;

j. CL 316243 (R,R-5-[2-[[2-(3-chlorophenyl)-2-hydroxyethyl]amino]propyl]-1,3-benzodioxole-2,2-dicarboxylate) as disclosed in Berlan et al. (1994) *J. Pharmacol. Exp. Ther.* 268: 1444–51 or acids, salts, esters, amides, prodrugs, active metabolites, and other derivatives thereof;

k. Compounds having 3 adrenergic agonist activity as disclosed in U.S. Patent Application 20030018061 or acids, salts, esters, amides, prodrugs, active metabolites, and other derivatives thereof;

l. ICI 215,001 HCl ((S)-4-[2-Hydroxy-3-phenoxypropyl-aminoethoxy]phenoxyacetic acid hydrochloride) as disclosed in Howe (1993) Drugs Future 18: 529 and available from AstraZeneca/ICI Labs or acids, salts, enantiomers, analogs, esters, amides, prodrugs, active metabolites, and derivatives thereof;

m. ZD 7114 HCl (ICI D7114; (S)-4-[2-Hydroxy-3-phenoxypropyl-aminoethoxy]-N-(2-methoxyethyl)phenoxyacetamide HCl) as disclosed in Howe (1993) Drugs Future 18: 529 and available from AstraZeneca/ICI Labs or acids, salts, enantiomers, analogs, esters, amides, prodrugs, active metabolites, and derivatives thereof, n. Pindolol (1-(1H-Indol-4-yloxy)-3-[(1-methylethyl)amino]-2-propanol) as disclosed in Blin et al (1994) Mol.Pharmacol. 44: 1094 or acids, salts, enantiomers, analogs, esters, amides, prodrugs, active metabolites, and derivatives thereof;

o. (S)-(–)-Pindolol ((S)-1-(1H-indol-4-yloxy)-3-[(1-methylethyl)amino]-2-propanol) as disclosed in Walter et al (1984) Naunyn-Schmied. Arch. Pharmacol. 327: 159 and Kalkman (1989) Eur. J. Pharmacol. 173: 121 or acids, salts, enantiomers, analogs, esters, amides, prodrugs, active metabolites, and derivatives thereof;

p. SR 59230A HCl (1-(2-Ethylphenoxy)-3-[[(1S)-1,2,3,4-tetrahydro-1-naphthalenyl]amino]-(2S)-2-propanol hydrochloride) as disclosed in Manara et al. (1995) Pharmacol. Comm. 6: 253 and Manara et al. (1996) Br. J. Pharmacol. 117: 435 and available from Sanofi-Midy or acids, salts, enantiomers, analogs, esters, amides, prodrugs, active metabolites, and derivatives thereof, q. SR 58611 (N[2s]7-carb-ethoxymethoxy-1,2,3,4-tetrahydronaphth]-(2r)-2-hydroxy-2(3-chlorophenyl) ethamine hydrochloride) as disclosed in Gauthier et al. (1999) J. Pharmacol. Exp. Ther. 290: 687–693 and available from Sanofi Research; and r. YM178 available from Yamanouchi Pharmaceutical Co. or acids, salts, esters, amides, prodrugs, active metabolites, and other derivatives thereof.

The identification of further compounds that have $\beta_3$ adrenergic agonist activity and would therefore be useful in the present invention can be determined by performing radioligand binding assays and/or contractility studies as described by Zilberfarb et al. (1997) *J. Cell Sci.* 110: 801–807; Takeda et al. (1999) *J. Pharmacol. Exp. Ther.* 288: 1367–1373; and Gauthier et al. (1999) *J. Pharmacol. Exp. Ther.* 290: 687–693.

Further, agents for use as additional therapeutic agents include sodium channel modulators, such as TTX-R sodium channel modulators and/or activity dependent sodium channel modulators. TTX-R sodium channel modulators for use in the present invention include but are not limited to compounds that modulate or interact with Nav1.8 and/or Nav1.9 channels.

Sodium channel modulators suitable for use as in the practice of the invention include, but are not limited to propionamides such as Ralfinamide (NW-1029) (as disclosed in U.S. Pat. Nos. 5,236,957 and 5,391,577), which is also known as (+)-2(S)-[4-(2-Fluorobenzyloxy)benzylamino]propionamide and safinamide (as disclosed in U.S. Pat. Nos. 5,236,957 and 5,391,577), which is also known as 2(S)-[4-(3-Fluorobenzyloxy)benzylamino]propionamide methanesulfonate Further sodium channel modulators include for example, N-phenylalkyl substituted α-amino carboxamide derivatives in addition to Ralfmamide and Salfmamide as disclosed in U.S. Pat. No. 5,236,957; Other N-phenylalkyl substituted α-amino carboxamide derivatives in addition to Ralfinamide and Salfinamide as disclosed in U.S. Pat. No. 5,391,577; Substituted 2-benzylamino-2-phenyl-acetamide compounds as disclosed in U.S. Pat. No. 6,303,819; aryldiazines and aryltriazines such as: sipatrigine (BW-619C; as disclosed in U.S. Pat. No. 5,684,005), which is also known as 4-Amino-2-(4-methylpiperazin-1-yl)-5-(2,3,5-trichlorophenyl)pyrimidine; 2-(4-Methylpiperazin-1-yl)-5-(2,3,5-trichlorophenyl)pyrimidine-4-amine; lamotrigine (as disclosed in U.S. Pat. No. 4,602,017), which is also known as 6-(2,3-Dichlorophenyl)-1,2,4-triazine-3,5-diamine; GW-273293 (as disclosed in U.S. Pat. No. 6,599,905), which is also known as 3-(2,3,5-Trichlorophenyl)pyrazine-2,6-diamine; 4030W92 (as disclosed in U.S. Pat. No. 6,124,308), which is also known as 5-(2,3-Dichlorophenyl)-6-(fluoromethyl)pyrimidine-2,4-diamine; Carbamazepine (as disclosed in U.S. Pat. No. 2,948,718), which is also known as 5H-Dibenz[d,f]azepine-5-carboxamide; Oxcarbazepine (as disclosed in U.S. Pat. No. 3,642,775), which is also known as 10-Oxo-10,11-dihydro-5H-dibenz[b,f]azepine-5-carboxamide; licarbazepine (as disclosed in DE 2011045), which is also known as (±)-10-Hydroxy-10,11-dihydro-5H-dibenz[b,f]azepine-5-carboxamide; BIA-2-093 (as disclosed in U.S. Pat. No. 5,753,646), which is also known as Acetic acid 5-carbamoyl-10,11-dihydro-5H-dibenzo[b,f]azepin-10(S)-yl ester; ADCI (as disclosed in U.S. Pat. No. 5,196,415), which is also known as (±)-5,10-Imino-10,11-dihydro-5H-dibenzo[a,d]cycloheptene-5-carboxamide; Phenytoin sodium (as disclosed in U.S. Pat. No. 2,409,754) and OROS®-Phenytoin (as disclosed in U.S. Pat. No. 4,260,769), which are also known as 5,5-Diphenylhydantoin sodium salt and 5,5-Diphenyl-2,4-imidazolidinedione salt; Fosphenytoin sodium (as disclosed in U.S. Pat. No. 4,260,769) and phosphenytoin sodium, which are also known as 3-(Hydroxymethyl)-5,5-diphenylhydantoin phosphate ester disodium salt and 5,5-Diphenyl-3-[(phosphonooxy)methyl]-2,4-imidazolidinedione disodium salt; Pilsicainide hydrochloride and analogs thereof (as disclosed in U.S. Pat. No. 4,564,624), which is also known as N-(2,6-Dimethylphenyl)-8-pyrrolizidineacetamide hydrochloride; N-(2,6-Dimethylphenyl)-1-azabicyclo[3.3.0]octane-5-acetamide hydrochloride; Tocainide (as disclosed in DE 2235745), which is also known as 2-Amino-N-(2,6-dimethylphenyl)propananide hydrochloride; Flecainide (as disclosed in U.S. Pat. No. 3,900,481), which is also known as N-(2-Piperidylmethyl)-2,5-bis(2,2,2-trifluoroethoxy)benzamide monoacetate; mexiletine hydrochloride (as disclosed in U.S. Pat. No. 3,954,872), which is also known as 1-(2,6-Dimethylphenoxy)-2-propanamine hydrochloride; Ropivacaine hydrochloride (as disclosed in PCT Publication No. WO 85/00599), which is also known as (–)-(S)-N-(n-Propyl)piperidine-2-carboxylic acid 2,6-xylidide hydrochloride monohydrate; (–)-(S)-N-(2,6-Dimethylphenyl)-1-propylpiperidine-2-carboxamide hydrochloride monohydrate; (–)-(S)-1-Propyl-2',6'-pipecoloxylidide hydrochloride monohydrate; Lidocaine (as disclosed in U.S. Pat. No. 2,441,498), which is also known as 2-(diethylamino)-N-(2,6-dimethylphenyl)acetamide; mepivacaine (as disclosed in U.S. Pat. No. 2,799,679), which is also known as N-(2,6-dimethylphenyl)-1-methyl-2-piperidinecarboxamide; bupivacaine (as disclosed in U.S. Pat. No. 2,955,111), which is also known as 1-butyl-N-(2,6-dimethylphenyl)-2-piperidinecarboxamide; Prilocaine (as disclosed in U.S. Pat. No. 3,160,662), also known as N-(2-methylphenyl)-2-(propylamino) propanamide; etidocaine (as disclosed in U.S. Pat. No. 3,812,147), which is also known as N-(2,6-dimethylphenyl)-1-methyl-2-piperidinecarboxamide; tetracaine (as disclosed in U.S. Pat. No. 1,889,645), which is also known as 4-(butylamino)benzoic acid 2-(diethylamino)ethyl ester; dibucaine (as disclosed in U.S. Pat. No. 1,825,623), which is also known as 2-butoxy-N-[2-(diethylamino)-ethyl]-4-quinolinecarboxamide; Soretolide, which is also known as 2,6-Dimethyl-N-(5-methylisozaxol-3-yl)benzamide; RS-132943 (as disclosed in U.S. Pat. No. 6,110,937), which is also known as 3(S)-(4-Bromo-2,6-dimethylphenoxymethyl)-1-methylpiperidine hydrochloride The identification of other agents that have affinity for TTX-R sodium channels or proteins associated with TTX-R sodium channels and would be useful in the present invention can be determined by methods that measure functional TTX-R channel activity such as sodium flux as disclosed in Stallcup, WB (1979) J. Physiol. 286: 525–40 or electrophysiological approaches as disclosed in Weiser and Wilson (2002) *Mol. Pharmacol.* 62: 433–438. The identification of other agents that exhibit activity-dependent modulation of sodium channels and would be useful in the present invention can be determined by methods as disclosed in Li et al., (1999) *Molecular Pharmacology* 55:134–141.

Further, agents for use as additional therapeutic agents include "Cav2.2 subunit calcium channel modulators" which are capable of binding to the Cav2.2 subunit of a calcium channel to produce a physiological effect, such as opening, closing, blocking, up-regulating expression, or down-regulating expression of the channel. Unless otherwise indicated, the term "Cav2.2 subunit calcium channel modulator" is intended to include amino acid compounds, peptide, nonpeptide, peptidomimetic, small molecular weight organic compounds, and other compounds that modulate or interact with the Cav2.2 subunit of a calcium channel (e.g., a binding event) or proteins associated with the Cav2.2 subunit of a calcium channel (e.g., a binding event) such as anchor proteins, as well as salts, esters, amides, prodrugs, active metabolites, and other derivatives thereof. Further, it is understood that any salts, esters, amides, prodrugs, active metabolites or other derivatives are pharmaceutically acceptable as well as pharmacologically active.

Cav2.2 subunit calcium channel modulator useful as an additional therapeutic agent in the practice of the invention include, but are not limited to:

a. ω-conotoxin GVIA or a salt, enantiomer, analog, ester, amide, prodrug, active metabolite, or derivative thereof;

b. ω-conotoxin MVIIA or a salt, enantiomer, analog, ester, amide, prodrug, active metabolite, or derivative thereof;

c. ω-conotoxin CNVIIA or a salt, enantiomer, analog, ester, amide, prodrug, active metabolite, or derivative thereof;

d. ω-conotoxin CVIID or a salt, enantiomer, analog, ester, amide, prodrug, active metabolite, or derivative thereof;

e. ω-conotoxin AM336 or a salt, enantiomer, analog, ester, amide, prodrug, active metabolite, or derivative thereof;

f. Cilnidipine or a salt, enantiomer, analog, ester, amide, prodrug, active metabolite, or derivative thereof;

g. Amlodipine or a salt, enantiomer, analog, ester, amide, prodrug, active metabolite, or derivative thereof;

h. L-cysteine derivative 2A or a salt, enantiomer, analog, ester, amide, prodrug, active metabolite, or derivative thereof;

i. ω-agatoxin IVA or a salt, enantiomer, analog, ester, amide, prodrug, active metabolite, or derivative thereof;
j. N,N-dialkyl-dipeptidylamines or a salt, enantiomer, analog, ester, amide, prodrug, active metabolite, or derivative thereof;
k. Levetiracetam or a salt, enantiomer, analog, ester, amide, prodrug, active metabolite, or derivative thereof; and
l. Ziconotide (SNX-111) or a salt, enantiomer, analog, ester, amide, prodrug, active metabolite, or derivative thereof;
m. (S)-alpha-ethyl-2-oxo-1-pyrrolidineacetamide (illustrated below) and disclosed in U.S. Pat. Nos. 4,943, 639, 4,837,223, and 4,696,943, or a salt, enantiomer, analog, ester, amide, prodrug, active metabolite, or derivative, thereof;
n. Substituted peptidylamines as disclosed in PCT Publication No. WO 98/54123, or a salt, enantiomer, analog, ester, amide, prodrug, active metabolite, or derivative, thereof;
o. PD-173212 or a salt, enantiomer, analog, ester, amide, prodrug, active metabolite, or derivative, thereof;
p. Reduced dipeptide analogues as disclosed in U.S. Pat. No. 6,316,440 and PCT Publication No. WO 00/06559, or a salt, enantiomer, analog, ester, amide, prodrug, active metabolite, or derivative, thereof;
q. Amino acid derivatives as disclosed in PCT Publication No. WO 99/02146, or a salt, enantiomer, analog, ester, amide, prodrug, active metabolite, or derivative, thereof;
r. Benzazepine derivatives as disclosed in Japanese Publication No. JP 2002363163, or a salt, enantiomer, analog, ester, amide, prodrug, active metabolite, or derivative, thereof;
s. Compounds disclosed in PCT Publication No. WO 02/36567, or a salt, enantiomer, analog, ester, amide, prodrug, active metabolite, or derivative, thereof;
t. Compounds disclosed in PCT Publication No. WO 03/018561, or a salt, enantiomer, analog, ester, amide, prodrug, active metabolite, or derivative, thereof;
u. Compounds disclosed in U.S. Patent Publication No. 2004009991 and PCT Publication No. WO 02/22588, or a salt, enantiomer, analog, ester, amide, prodrug, active metabolite, or derivative, thereof;
v. Dihydropyridine derivatives as disclosed in U.S. Pat. No. 6,610,717, U.S. Patent Publication No. 2002193605, and PCT Publication No. WO 00/78720, or a salt, enantiomer, analog, ester, amide, prodrug, active metabolite, or derivative, thereof;
w. Diarylalkene and diaryalkane derivatives as disclosed in PCT Publication No. WO 03/018538, or a salt, enantiomer, analog, ester, amide, prodrug, active metabolite, or derivative, thereof; and Additional Cav2.2 subunit calcium channel modulator useful as an additional therapeutic agent in the practice of the invention include, but are not limited to non-peptide, and peptidomimetic drug-like molecules that bind to Cav2.2-containing calcium channels as disclosed in Lewis et al. (2000) *J. Biol. Chem.* 10: 35335–44; Smith et al. (2002) *Pain* 96: 119–27; Takahara et al. (2002) *Eur. J. Pharmacol.* 434: 43–7; Favreau et al. (2001) *Biochemistry*, 40: 14567–575; Seko et al. (2001) *Bioorg. Med. Chem. Lett.* 11: 2067–70; Hu et al. (2000) *Bioorg. Med. Chem. Lett.* 8: 1203–12; Lew et al. (1997) *J. Biol. Chem.* 272: 12014–23. It is understood that the present invention also encompasses any pharmaceutically acceptable, pharmacologically active salts, enantiomers, analogs, esters, amides, prodrugs, active metabolites, and derivatives of the aforementioned compounds.

The identification of other agents that have affinity for the Cav2.2 subunit of a calcium channel and would be useful in the present invention can be determined by performing Cav2.2 subunit binding affinity, electrophysiolgic, and/or other screening methods as described in Feng et al. (*J. Biol. Chem.*, 278: 20171–20178, 2003), Feng et al. (*J. Biol. Chem.*, 276: 15728–15735, 2001), Favreau et al. (*Biochemistry*, 40: 14567–575, 2001), and/or U.S. Pat. No. 6,387,897 assigned to NeuroMed Technologies Inc The term "spasmolytic" (also known as "antispasmodic") is used in its conventional sense to refer to a compound that relieves or prevents muscle spasms, especially of smooth muscle. Unless otherwise indicated, the term "spasmolytic" is intended to include spasmolytic agents as disclosed further herein, as well as acids, salts, esters, amides, prodrugs, active metabolites, and other derivatives thereof. Further, it is understood that any salts, esters, amides, prodrugs, active metabolites or other derivatives are pharmaceutically acceptable as well as pharmacologically active. In general, spasmolytics have been implicated as having efficacy in the treatment of bladder disorders (See. e.g., Takeda et al. (2000) *J. Pharmacol. Exp. Ther.* 293: 939–45).

Compounds that have been identified as spasmolytic agents and are useful in the present invention include, but are not limited to:
a. α-α-diphenylacetic acid-4-(N-methyl-piperidyl) esters as disclosed in U.S. Pat. No. 5,897,875 or acids, salts, enantiomers, analogs, esters, amides, prodrugs, active metabolites, and derivatives thereof;
b. Human and porcine spasmolytic polypeptides in glycosylated form and variants thereof as disclosed in U.S. Pat. No. 5,783,416 or acids, salts, enantiomers, analogs, esters, amides, prodrugs, active metabolites, and derivatives thereof;
c. Dioxazocine derivatives as disclosed in U.S. Pat. No. 4,965,259 or acids, salts, enantiomers, analogs, esters, amides, prodrugs, active metabolites, and derivatives thereof;
d. Quaternary 6,11-dihydro-dibenzo-[b,e]-thiepine-11-N-alkylnorscopine ethers as disclosed in U.S. Pat. No. 4,608,377 or acids, salts, enantiomers, analogs, esters, amides, prodrugs, active metabolites, and derivatives thereof;
e. Quaternary salts of dibenzo[1,4]diazepinones, pyrido-[1,4]benzodiazepinones, pyrido[1,5]benzodiazepinones as disclosed in U.S. Pat. No. 4,594,190 or acids, salts, enantiomers, analogs, esters, amides, prodrugs, active metabolites, and derivatives thereof;
f. Endo-8,8-dialkyl-8-azoniabicyclo (3.2.1) octane-6,7-exo-epoxy-3-alkyl-carboxylate salts as disclosed in U.S. Pat. No. 4,558,054 or acids, salts, enantiomers, analogs, esters, amides, prodrugs, active metabolites, and derivatives thereof;
g. Pancreatic spasmolytic polypeptides as disclosed in U.S. Pat. No. 4,370,317 or acids, salts, enantiomers, analogs, esters, amides, prodrugs, active metabolites, and derivatives thereof;
h. Triazinones as disclosed in U.S. Pat. No. 4,203,983 or acids, salts, enantiomers, analogs, esters, amides, prodrugs, active metabolites, and derivatives thereof;
i. 2-(4-Biphenylyl)-N-(2-diethylamino alkyl)propionarnide as disclosed in U.S. Pat. No. 4,185,124 or acids, salts, enantiomers, analogs, esters, amides, prodrugs, active metabolites, and derivatives thereof;

j. Piperazino-pyrimidines as disclosed in U.S. Pat. No. 4,166,852 or acids, salts, enantiomers, analogs, esters, amides, prodrugs, active metabolites, and derivatives thereof;

k. Aralkylamino carboxylic acids as disclosed in U.S. Pat. No. 4,163,060 or acids, salts, enantiomers, analogs, esters, amides, prodrugs, active metabolites, and derivatives thereof;

l. Aralkylamino sulfones as disclosed in U.S. Pat. No. 4,034,103 or acids, salts, enantiomers, analogs, esters, amides, prodrugs, active metabolites, and derivatives thereof;

m. Smooth muscle spasmolytic agents as disclosed in U.S. Pat. No. 6,207,852 or acids, salts, enantiomers, analogs, esters, amides, prodrugs, active metabolites, and derivatives thereof; and n. Papaverine or acids, salts, enantiomers, analogs, esters, amides, prodrugs, active metabolites, and derivatives thereof.

The identification of further compounds that have spasmolytic activity and would therefore be useful in the present invention can be determined by performing bladder strip contractility studies as described in U.S. Pat. No. 6,207,852; Noronha-Blob et al. (1991) *J. Pharmacol. Exp. Ther.* 256: 562–567; and/or Kachur et al. (1988) *J. Pharmacol Exp. Ther.* 247: 867–872.

The term "neurokinin receptor antagonist" is used in its conventional sense to refer to a compound that binds to and antagonizes neurokinin receptors. Unless otherwise indicated, the term "neurokinin receptor antagonist" is intended to include neurokinin receptor antagonist agents as disclosed further herein, as well as acids, salts, esters, amides, prodrugs, active metabolites, and other derivatives thereof. Further, it is understood that any salts, esters, amides, prodrugs, active metabolites or other derivatives are pharmaceutically acceptable as well as pharmacologically active.

Suitable neurokinin receptor antagonists for use in the present invention that act on the NK1 receptor include, but are not limited to: 1-imino-2-(2-methoxy-phenyl)-ethyl)-7,7-diphenyl-4-perhydroisoindolone (3aR,7aR) ("RP 67580"); 2S,3S-cis-3-(2-methoxybenzylamino)-2-benzhydrylquinuclidine ("CP 96,345"); and (aR,9R)-7-[3,5-bis(trifluoromethyl)benzyl]-8,9,10,11-tetrahydro-9-methyl-5-(4-methylphenyl)-7H-[1,4]diazocino[2,1-g] [1,7]naphthyridine-6,13-dione)("TAK-637"). Suitable neurokinin receptor antagonists for use in the present invention that act on the NK2 receptor include but are not limited to: ((S)-N-methyl-N-4-(4-acetylamino-4-phenylpiperidino)-2-(3,4-dichlorophenyl)butylbenzamide ("SR 48968"); Met-Asp-Trp-Phe-Dap-Leu ("MEN 10,627"); and cyc(Gln-Trp-Phe-Gly-Leu-Met) ("L 659,877"). Suitable neurokinin receptor antagonists for use in the present invention also include acids, salts, esters, amides, prodrugs, active metabolites, and other derivatives of any of the agents mentioned above. The identification of further compounds that have neurokinin receptor antagonist activity and would therefore be useful in the present invention can be determined by performing binding assay studies as described in Hopkins et al. (1991) *Biochem. Biophys. Res. Comm.* 180: 1110–1117; and Aharony et al. (1994) *Mol. Pharmacol.* 45: 9–19.

The term "bradykinin receptor antagonist" is used in its conventional sense to refer to a compound that binds to and antagonizes bradykinin receptors. Unless otherwise indicated, the term "bradykinin receptor antagonist" is intended to include bradykinin receptor antagonist agents as disclosed further herein, as well as acids, salts, esters, amides, prodrugs, active metabolites, and other derivatives thereof. Further, it is understood that any salts, esters, amides, prodrugs, active metabolites or other derivatives are pharmaceutically acceptable as well as pharmacologically active.

Suitable bradykinin receptor antagonists for use in the present invention that act on the B1 receptor include but are not limited to: des-arg10HOE 140 (available from Hoechst Pharmaceuticals) and des-Arg9bradykinin (DABK). Suitable bradykinin receptor antagonists for use in the present invention that act on the B2 receptor include but are not limited to: D-Phe7-BK; D-Arg-(Hyp3-Thi5,8-D-Phe7)-BK ("NPC 349"); D-Arg-(Hyp3-D-Phe7)-BK ("NPC 567"); D-Arg-(Hyp3-Thi5-D-Tic7-Oic8)-BK ("HOE 140"); H-DArg-Arg-Pro-Hyp-Gly-Thi-c(Dab-DTic-Oic-Arg)c (7gamma-10alpha)("MEN 11270"); H-DArg-Arg-Pro-Hyp-Gly-Thi-Ser-DTic-Oic-Arg-OH("Icatibant"); (E)-3-(6-acetamido-3-pyridyl)-N-[N-[2, 4-dichloro-3-[(2-methyl-8-quinolinyl)oxymethyl]phenyl]-N-methylaminocarbonylmethyl]acrylamide ("FR 173567"); and WIN 64338. These compounds are more fully described in Perkins, M. N., et. al., Pain, supra; Dray, A., et. al., *Trends Neurosci.*, supra; and Meini et al. (2000) *Eur. J. Pharmacol.* 388: 177–82. Suitable neurokinin receptor antagonists for use in the present invention also include acids, salts, esters, amides, prodrugs, active metabolites, and other derivatives of any of the agents mentioned above. The identification of further compounds that have bradykinin receptor antagonist activity and would therefore be useful in the present invention can be determined by performing binding assay studies as described in Manning et al. (1986) *J. Pharmacol. Exp. Ther.* 237: 504 and U.S. Pat. No. 5,686,565.

The term "nitric oxide donor" is used in its conventional sense to refer to a compound that releases free nitric oxide when administered to a patient. Unless otherwise indicated, the term "nitric oxide donor" is intended to include nitric oxide donor agents as disclosed further herein, as well as acids, salts, esters, amides, prodrugs, active metabolites, and other derivatives thereof. Further, it is understood that any salts, esters, amides, prodrugs, active metabolites or other derivatives are pharmaceutically acceptable as well as pharmacologically active.

Suitable nitric oxide donors for the practice of the present invention include but are not limited to:

a. Nitroglycerin or acids, salts, enantiomers, analogs, esters, amides, prodrugs, active metabolites, and derivatives thereof;

b. Sodium nitroprusside or acids, salts, enantiomers, analogs, esters, amides, prodrugs, active metabolites, and derivatives thereof;

c. FK 409 (NOR-3) or acids, salts, enantiomers, analogs, esters, amides, prodrugs, active metabolites, and derivatives thereof;

d. FR 144420 (NOR-4) or acids, salts, enantiomers, analogs, esters, amides, prodrugs, active metabolites, and derivatives thereof;

e. 3-morpholinosydnonimine or acids, salts, enantiomers, analogs, esters, amides, prodrugs, active metabolites, and derivatives thereof;

f. Linsidomine chlorohydrate ("SIN-1") or acids, salts, enantiomers, analogs, esters, amides, prodrugs, active metabolites, and derivatives thereof;

g. S-nitroso-N-acetylpenicillamine ("SNAP") or acids, salts, enantiomers, analogs, esters, amides, prodrugs, active metabolites, and derivatives thereof;

h. AZD3582 (CINOD lead compound, available from NicOx S.A.) or acids, salts, enantiomers, analogs, esters, amides, prodrugs, active metabolites, and derivatives thereof;

i. NCX 4016 (available from NicOx S.A.) or acids, salts, enantiomers, analogs, esters, amides, prodrugs, active metabolites, and derivatives thereof;
j. NCX 701 (available from NicOx S.A.) or acids, salts, enantiomers, analogs, esters, amides, prodrugs, active metabolites, and derivatives thereof;
k. NCX 1022 (available from NicOx S.A.) or acids, salts, enantiomers, analogs, esters, amides, prodrugs, active metabolites, and derivatives thereof;
l. HCT 1026 (available from NicOx S.A.) or acids, salts, enantiomers, analogs, esters, amides, prodrugs, active metabolites, and derivatives thereof;
m. NCX 1015 (available from NicOx S.A.) or acids, salts, enantiomers, analogs, esters, amides, prodrugs, active metabolites, and derivatives thereof;
n. NCX 950 (available from NicOx S.A.) or acids, salts, enantiomers, analogs, esters, amides, prodrugs, active metabolites, and derivatives thereof;
o. NCX 1000 (available from NicOx S.A.) or acids, salts, enantiomers, analogs, esters, amides, prodrugs, active metabolites, and derivatives thereof;
p. NCX 1020 (available from NicOx S.A.) or acids, salts, enantiomers, analogs, esters, amides, prodrugs, active metabolites, and derivatives thereof;
q. AZD 4717 (available from NicOx S.A.) or acids, salts, enantiomers, analogs, esters, amides, prodrugs, active metabolites, and derivatives thereof;
r. NCX 1510/NCX 1512 (available from NicOx S.A.) or acids, salts, enantiomers, analogs, esters, amides, prodrugs, active metabolites, and derivatives thereof;
s. NCX 2216 (available from NicOx S.A.) or acids, salts, enantiomers, analogs, esters, amides, prodrugs, active metabolites, and derivatives thereof;
t. NCX 4040 (available from NicOx S.A.) or acids, salts, enantiomers, analogs, esters, amides, prodrugs, active metabolites, and derivatives thereof;
u. Nitric oxide donors as disclosed in U.S. Pat. No. 5,155,137 or acids, salts, enantiomers, analogs, esters, amides, prodrugs, active metabolites, and derivatives thereof;
v. Nitric oxide donors as disclosed in U.S. Pat. No. 5,366,997 or acids, salts, enantiomers, analogs, esters, amides, prodrugs, active metabolites, and derivatives thereof;
w. Nitric oxide donors as disclosed in U.S. Pat. No. 5,405,919 or acids, salts, enantiomers, analogs, esters, amides, prodrugs, active metabolites, and derivatives thereof;
x. Nitric oxide donors as disclosed in U.S. Pat. No. 5,650,442 or acids, salts, enantiomers, analogs, esters, amides, prodrugs, active metabolites, and derivatives thereof;
y. Nitric oxide donors as disclosed in U.S. Pat. No. 5,700,830 or acids, salts, enantiomers, analogs, esters, amides, prodrugs, active metabolites, and derivatives thereof;
z. Nitric oxide donors as disclosed in U.S. Pat. No. 5,632,981 or acids, salts, enantiomers, analogs, esters, amides, prodrugs, active metabolites, and derivatives thereof;
aa. Nitric oxide donors as disclosed in U.S. Pat. No. 6,290,981 or acids, salts, enantiomers, analogs, esters, amides, prodrugs, active metabolites, and derivatives thereof;
bb. Nitric oxide donors as disclosed in U.S. Pat. No. 5,691,423 or acids, salts, enantiomers, analogs, esters, amides, prodrugs, active metabolites, and derivatives thereof;
cc. Nitric oxide donors as disclosed in U.S. Pat. No. 5,721,365 or acids, salts, enantiomers, analogs, esters, amides, prodrugs, active metabolites, and derivatives thereof;
dd. Nitric oxide donors as disclosed in U.S. Pat. No. 5,714,511 or acids, salts, enantiomers, analogs, esters, amides, prodrugs, active metabolites, and derivatives thereof;
ee. Nitric oxide donors as disclosed in U.S. Pat. No. 6,511,911 or acids, salts, enantiomers, analogs, esters, amides, prodrugs, active metabolites, and derivatives thereof; and
ff. Nitric oxide donors as disclosed in U.S. Pat. No. 5,814,666.

The identification of further compounds that have nitric oxide donor activity and would therefore be useful in the present invention can be determined by release profile and/or induced vasospasm studiesas described in U.S. Pat. Nos. 6,451,337 and 6,358,536, as well as Moon (2002) *IBJU Int.* 89: 942–9 and Fathian-Sabet et al. (2001) *J. Urol.* 165: 1724–9.

Subject, as used herein, refers to animals such as mammals, including, but not limited to, primates (e.g., humans), cows, sheep, goats, horses, pigs, dogs, cats, rabbits, guinea pigs, rats, mice or other bovine, ovine, equine, canine, feline, rodent or murine species.

As used herein, treating and treatment refer to a reduction in at least one symptom selected from urinary frequency, urinary urgency, urinary urge incontinence, nocturia and enuresis, which is associated with lower urinary tract disorder.

As used herein, therapeutically effective amount refers to an amount sufficient to elicit the desired biological response. In the present invention the desired biological response is a reduction (complete or partial) of at least one symptom associated with the lower urinary tract disorder being treated wherein the symptom is selected from urinary frequency, urinary urgency, urinary urge incontinence, nocturia and enuresis. As with any treatment, particularly treatment of a multi-symptom disorder, for example, overactive bladder, it is advantageous to treat as many disorder-related symptoms which the subject experiences.

Pharmaceutically acceptable carrier, includes pharmaceutical diluents, excipients or carriers suitably selected with respect to the intended form of administration, and consistent with conventional pharmaceutical practices. For example, solid carriers/diluents include, but are not limited to, a gum, a starch (e.g., corn starch, pregelatinized starch), a sugar (e.g., lactose, mannitol, sucrose, dextrose), a cellulosic material (e.g., microcrystalline cellulose), an acrylate (e.g., polymethylacrylate), calcium carbonate, magnesium oxide, talc, or mixtures thereof.

Pharmaceutically acceptable carriers can be aqueous or non-aqueous solvents. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media.

Modes of Adminstration

The compounds for use in the method or kits of the invention can be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intraduodenal, intrathecal, subcutaneous, intramuscular, intradermal, intra-arterial, intravenous, inhalation, and topical administration.

Suitable compositions and dosage forms include tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. Further, those of ordinary skill in the art can readily deduce that suitable formulations involving these compositions and dosage forms, including those formulations as described elsewhere herein.

The term intravesical administration is used herein in its conventional sense to mean delivery of a drug directly into the bladder.

For oral administration the compounds can be of the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets can be coated using suitable methods and coating materials such as OPADRY® film coating systems available from Colorcon, West Point, Pa. (e.g., OPADRY® OY Type, OY-C Type, Organic Enteric OY-P Type, Aqueous Enteric OY-A Type, OY-PM Type and OPADRY® White, 32K18400). Liquid preparation for oral administration can be in the form of solutions, syrups or suspensions. The liquid preparations can be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Tablets may be manufactured using standard tablet processing procedures and equipment. One method for forming tablets is by direct compression of a powdered, crystalline or granular composition containing the active agent(s), alone or in combination with one or more carriers, additives, or the like. As an alternative to direct compression, tablets can be prepared using wet-granulation or dry-granulation processes. Tablets may also be molded rather than compressed, starting with a moist or otherwise tractable material; however, compression and granulation techniques are preferred.

The dosage form may also be a capsule, in which case the active agent-containing composition may be encapsulated in the form of a liquid or solid (including particulates such as granules, beads, powders or pellets). Suitable capsules can be hard or soft, and are generally made of gelatin, starch, or a cellulosic material, with gelatin capsules preferred. Two-piece hard gelatin capsules are preferably sealed, such as with gelatin bands or the like. (See, for e.g., Remington: The Science and Practice of Pharmacy, supra), which describes materials and methods for preparing encapsulated pharmaceuticals. If the active agent-containing composition is present within the capsule in liquid form, a liquid carrier can be used to dissolve the active agent(s). The carrier should be compatible with the capsule material and all components of the pharmaceutical composition, and should be suitable for ingestion.

Transmucosal administration is carried out using any type of formulation or dosage unit suitable for application to mucosal tissue. For example, the selected active agent can be administered to the buccal mucosa in an adhesive tablet or patch, sublingually administered by placing a solid dosage form under the tongue, lingually administered by placing a solid dosage form on the tongue, administered nasally as droplets or a nasal spray, administered by inhalation of an aerosol formulation, a non-aerosol liquid formulation, or a dry powder, placed within or near the rectum ("transrectal" formulations), or administered to the urethra as a suppository, ointment, or the like.

Preferred buccal dosage forms will typically comprise a therapeutically effective amount of an active agent and a bioerodible (hydrolyzable) polymeric carrier that may also serve to adhere the dosage form to the buccal mucosa. The buccal dosage unit can be fabricated so as to erode over a predetermined time period, wherein drug delivery is provided essentially throughout. The time period is typically in the range of from about 1 hour to about 72 hours. Preferred buccal delivery preferably occurs over a time period of from about 2 hours to about 24 hours. Buccal drug delivery for short term use should preferably occur over a time period of from about 2 hours to about 8 hours, more preferably over a time period of from about 3 hours to about 4 hours. As needed buccal drug delivery preferably will occur over a time period of from about 1 hour to about 12 hours, more preferably from about 2 hours to about 8 hours, most preferably from about 3 hours to about 6 hours. Sustained buccal drug delivery will preferably occur over a time period of from about 6 hours to about 72 hours, more preferably from about 12 hours to about 48 hours, most preferably from about 24 hours to about 48 hours. Buccal drug delivery, as will be appreciated by those skilled in the art, avoids the disadvantages encountered with oral drug administration, e.g., slow absorption, degradation of the active agent by fluids present in the gastrointestinal tract and/or first-pass inactivation in the liver.

The amount of the active agent in the buccal dosage unit will of course depend on the potency of the agent and the intended dosage, which, in turn, is dependent on the particular individual undergoing treatment, the specific indication, and the like. The buccal dosage unit will generally contain from about 1.0 wt. % to about 60 wt. % active agent, preferably on the order of from about 1 wt. % to about 30 wt. % active agent. With regard to the bioerodible (hydrolyzable) polymeric carrier, it will be appreciated that virtually any such carrier can be used, so long as the desired drug release profile is not compromised, and the carrier is compatible with the active agents to be administered and any other components of the buccal dosage unit. Generally, the polymeric carrier comprises a hydrophilic (water-soluble and water-swellable) polymer that adheres to the wet surface of the buccal mucosa. Examples of polymeric carriers useful herein include acrylic acid polymers and co, e.g., those known as "carbomers" (Carbopol®, which may be obtained from B. F. Goodrich, is one such polymer). Other suitable polymers include, but are not limited to: hydrolyzed polyvinylalcohol; polyethylene oxides (e.g., Sentry Polyox® water soluble resins, available from Union Carbide); polyacrylates (e.g., Gantrez®, which may be obtained from GAF); vinyl polymers and copolymers; polyvinylpyrrolidone; dextran; guar gum; pectins; starches; and cellulosic polymers such as hydroxypropyl methylcellulose, (e.g., Methocel®, which may be obtained from the Dow Chemical Company), hydroxypropyl cellulose (e.g., Klucel®, which may also be obtained from Dow), hydroxypropyl cellulose ethers (see, e.g., U.S. Pat. No. 4,704,285 to Alderman), hydroxyethyl cellulose, carboxymethyl cellulose, sodium carboxymethyl cellulose, methyl cellulose, ethyl cellulose, cellulose acetate phthalate, cellulose acetate butyrate, and the like.

Other components can also be incorporated into the buccal dosage forms described herein. The additional components include, but are not limited to, disintegrants, diluents, binders, lubricants, flavoring, colorants, preservatives, and the like. Examples of disintegrants that may be used include, but are not limited to, cross-linked polyvinylpyrrolidones, such as crospovidone (e.g., Polyplasdone® XL, which may be obtained from GAF), cross-linked carboxylic methylcelluloses, such as croscarmelose (e.g., Ac-di-sol®, which may be obtained from FMC), alginic acid, and sodium carboxymethyl starches (e.g., Explotab®, which can be obtained from Edward Medell Co., Inc.), methylcellulose, agar bentonite and alginic acid. Suitable diluents include those which are generally useful in pharmaceutical formulations prepared using compression techniques, e.g., dicalcium phosphate dihydrate (e.g., Di-Tab®, which may be obtained from Stauffer), sugars that have been processed by cocrystallization with dextrin (e.g., co-crystallized sucrose and dextrin such as Di-Pak®, which may be obtained from Amstar), calcium phosphate, cellulose, kaolin, mannitol, sodium chloride, dry starch, powdered sugar and the like. Binders, if used, include those that enhance adhesion. Examples of such binders include, but are not limited to, starch, gelatin and sugars such as sucrose, dextrose, molasses, and lactose. Particularly preferred lubricants are stearates and stearic acid, and an optimal lubricant is magnesium stearate.

Sublingual and lingual dosage forms include tablets, creams, ointments, lozenges, pastes, and any other suitable dosage form where the active ingredient is admixed into a disintegrable matrix. The tablet, cream, ointment or paste for sublingual or lingual delivery comprises a therapeutically effective amount of the selected active agent and one or more conventional nontoxic carriers suitable for sublingual or lingual drug administration. The sublingual and lingual dosage forms of the present invention can be manufactured using conventional processes. The sublingual and lingual dosage units can be fabricated to disintegrate rapidly. The time period for complete disintegration of the dosage unit is typically in the range of from about 10 seconds to about 30 minutes, and optimally is less than 5 minutes.

Other components can also be incorporated into the sublingual and lingual dosage forms described herein. The additional components include, but are not limited to binders, disintegrants, wetting agents, lubricants, and the like. Examples of binders that can be used include water, ethanol, polyvinylpyrrolidone; starch solution gelatin solution, and the like. Suitable disintegrants include dry starch, calcium carbonate, polyoxyethylene sorbitan fatty acid esters, sodium lauryl sulfate, stearic monoglyceride, lactose, and the like. Wetting agents, if used, include glycerin, starches, and the like. Particularly preferred lubricants are stearates and polyethylene glycol. Additional components that may be incorporated into sublingual and lingual dosage forms are known, or will be apparent, to those skilled in this art (See, e.g., Remington: The Science and Practice of Pharmacy, supra).

With regard to transurethal administration, the formulation can comprise a urethral dosage form containing the active agent and one or more selected carriers or excipients, such as water, silicone, waxes, petroleum jelly, polyethylene glycol ("PEG"), propylene glycol ("PG"), liposomes, sugars such as mannitol and lactose, and/or a variety of other materials, with polyethylene glycol and derivatives thereof particularly preferred. A transurethral permeation enhancer can be included in the dosage from. Examples of suitable permeation enhancers include dimethylsulfoxide ("DMSO"), dimethyl formamide ("DMF"), N,N-dimethylacetamide ("DMA"), decylmethylsulfoxide ("C10 MSO"), polyethylene glycol monolaurate ("PEGML"), glycerol monolaurate, lecithin, the 1-substituted azacycloheptan-2-ones, particularly 1-n-dodecylcyclazacycloheptan-2-one (available under the trademark Azone® from Nelson Research & Development Co., Irvine, Calif.), SEPA® (available from Macrochem Co., Lexington, Mass.), surfactants as discussed above, including, for example, Tergitol®, Nonoxynol-9® and TWEEN-80®, and lower alkanols such as ethanol.

Transurethral drug administration, as explained in U.S. Pat. Nos. 5,242,391, 5,474,535, 5,686,093 and 5,773,020, can be carried out in a number of different ways using a variety of urethral dosage forms. For example, the drug can be introduced into the urethra from a flexible tube, squeeze bottle, pump or aerosol spray. The drug can also be contained in coatings, pellets or suppositories that are absorbed, melted or bioeroded in the urethra. In certain embodiments, the drug is included in a coating on the exterior surface of a penile insert. It is preferred, although not essential, that the drug be delivered from at least about 3 cm into the urethra, and preferably from at least about 7 cm into the urethra. Generally, delivery from at least about 3 cm to about 8 cm into the urethra will provide effective results in conjunction with the present method.

Urethral suppository formulations containing PEG or a PEG derivative can be conveniently formulated using conventional techniques, e.g., compression molding, heat molding or the like, as will be appreciated by those skilled in the art and as described in the pertinent literature and pharmaceutical texts. (See, e.g., Remington: The Science and Practice of Pharmacy, supra), which discloses typical methods of preparing pharmaceutical compositions in the form of urethral suppositories. The PEG or PEG derivative preferably has a molecular weight in the range of from about 200 to about 2,500 g/mol, more preferably in the range of from about 1,000 to about 2,000 g/mol. Suitable polyethylene glycol derivatives include polyethylene glycol fatty acid esters, for example, polyethylene glycol monostearate, polyethylene glycol sorbitan esters, e.g., polysorbates, and the like. Depending on the particular active agent, urethral suppositories may contain one or more solubilizing agents effective to increase the solubility of the active agent in the PEG or other transurethral vehicle.

It may be desirable to deliver the active agent in a urethral dosage form that provides for controlled or sustained release of the agent. In such a case, the dosage form can comprise a biocompatible, biodegradable material, typically a biodegradable polymer. Examples of such polymers include polyesters, polyalkylcyanoacrylates, polyorthoesters, polyanhydrides, albumin, gelatin and starch. As explained, for example, in PCT Publication No. WO 96/40054, these and other polymers can be used to provide biodegradable microparticles that enable controlled and sustained drug release, in turn minimizing the required dosing frequency.

The urethral dosage form will preferably comprise a suppository that is from about 2 to about 20 mm in length, preferably from about 5 to about 10 mm in length, and less than about 5 mm in width, preferably less than about 2 mm in width. The weight of the suppository will typically be in the range of from about 1 mg to about 100 mg, preferably in the range of from about 1 mg to about 50 mg. However, it will be appreciated by those skilled in the art that the size of the suppository can and will vary, depending on the potency of the drug, the nature of the formulation, and other factors.

Transurethral drug delivery may involve an "active" delivery mechanism such as iontophoresis, electroporation or phonophoresis. Devices and methods for delivering drugs in this way are well known in the art. Iontophoretically assisted drug delivery is, for example, described in PCT Publication No. WO 96/40054, cited above. Briefly, the active agent is driven through the urethral wall by means of an electric current passed from an external electrode to a second electrode contained within or affixed to a urethral probe.

Preferred transrectal dosage forms can include rectal suppositories, creams, ointments, and liquid formulations (enemas). The suppository, cream, ointment or liquid formulation for transrectal delivery comprises a therapeutically effective amount of the selected phosphodiesterase inhibitor and one or more conventional nontoxic carriers suitable for transrectal drug administration. The transrectal dosage forms of the present invention can be manufactured using conventional processes. The transrectal dosage unit can be fabricated to disintegrate rapidly or over a period of several hours. The time period for complete disintegration is preferably in the range of from about 10 minutes to about 6 hours, and optimally is less than about 3 hours.

Other components can also be incorporated into the transrectal dosage forms described herein. The additional components include, but are not limited to, stiffening agents, antioxidants, preservatives, and the like. Examples of stiffening agents that may be used include, for example, paraffin, white wax and yellow wax. Preferred antioxidants, if used, include sodium bisulfite and sodium metabisulfite.

Preferred vaginal or perivaginal dosage forms include vaginal suppositories, creams, ointments, liquid formulations, pessaries, tampons, gels, pastes, foams or sprays. The suppository, cream, ointment, liquid formulation, pessary, tampon, gel, paste, foam or spray for vaginal or perivaginal delivery comprises a therapeutically effective amount of the selected active agent and one or more conventional nontoxic carriers suitable for vaginal or perivaginal drug administration. The vaginal or perivaginal forms of the present invention can be manufactured using conventional processes as disclosed in Remington: The Science and Practice of Pharmacy, supra (see also drug formulations as adapted in U.S. Pat. Nos. 6,515,198; 6,500,822; 6,417,186; 6,416,779; 6,376,500; 6,355,641; 6,258,819; 6,172,062; and 6,086,909). The vaginal or perivaginal dosage unit can be fabricated to disintegrate rapidly or over a period of several hours. The time period for complete disintegration is preferably in the range of from about 10 minutes to about 6 hours, and optimally is less than about 3 hours.

Other components can also be incorporated into the vaginal or perivaginal dosage forms described herein. The additional components include, but are not limited to, stiffening agents, antioxidants, preservatives, and the like. Examples of stiffening agents that may be used include, for example, paraffin, white wax and yellow wax. Preferred antioxidants, if used, include sodium bisulfite and sodium metabisulfite.

The active agents can also be administered intranasally or by inhalation. Compositions for intranasal administration are generally liquid formulations for administration as a spray or in the form of drops, although powder formulations for intranasal administration, e.g., insufflations, nasal gels, creams, pastes or ointments or other suitable formulators can be used. For liquid formulations, the active agent can be formulated into a solution, e.g., water or isotonic saline, buffered or unbuffered, or as a suspension. Preferably, such solutions or suspensions are isotonic relative to nasal secretions and of about the same pH, ranging e.g., from about pH 4.0 to about pH 7.4 or, from about pH 6.0 to about pH 7.0. Buffers should be physiologically compatible and include, for example, phosphate buffers. Furthermore, various devices are available in the art for the generation of drops, droplets and sprays, including droppers, squeeze bottles, and manually and electrically powered intranasal pump dispensers. Active agent containing intranasal carriers can also include nasal gels, creams, pastes or ointments with a viscosity of, e.g., from about 10 to about 6500 cps, or greater, depending on the desired sustained contact with the nasal mucosal surfaces. Such carrier viscous formulations can be based upon, for example, alkylcelluloses and/or other biocompatible carriers of high viscosity well known to the art (see e.g., Remington: The Science and Practice of Pharmacy, supra). Other ingredients, such as preservatives, colorants, lubricating or viscous mineral or vegetable oils, perfumes, natural or synthetic plant extracts such as aromatic oils, and humectants and viscosity enhancers such as, e.g., glycerol, can also be included to provide additional viscosity, moisture retention and a pleasant texture and odor for the formulation. Formulations for inhalation may be prepared as an aerosol, either a solution aerosol in which the active agent is solubilized in a carrier (e.g., propellant) or a dispersion aerosol in which the active agent is suspended or dispersed throughout a carrier and an optional solvent. Non-aerosol formulations for inhalation can take the form of a liquid, typically an aqueous suspension, although aqueous solutions may be used as well. In such a case, the carrier is typically a sodium chloride solution having a concentration such that the formulation is isotonic relative to normal body fluid. In addition to the carrier, the liquid formulations can contain water and/or excipients including an antimicrobial preservative (e.g., benzalkonium chloride, benzethonium chloride, chlorobutanol, phenylethyl alcohol, thimerosal and combinations thereof), a buffering agent (e.g., citric acid, potassium metaphosphate, potassium phosphate, sodium acetate, sodium citrate, and combinations thereof), a surfactant (e.g., polysorbate 80, sodium lauryl sulfate, sorbitan monopalmitate and combinations thereof), and/or a suspending agent (e.g., agar, bentonite, microcrystalline cellulose, sodium carboxymethylcellulose, hydroxypropyl methylcellulose, tragacanth, veegum and combinations thereof). Non-aerosol formulations for inhalation can also comprise dry powder formulations, particularly insufflations in which the powder has an average particle size of from about 0.1 µm to about 50 µm, preferably from about 1 µm to about 25 µm.

One common system utilized for intrathecal administration is the APT Intrathecal treatment system available from Medtronic, Inc. APT Intrathecal uses a small pump that is surgically placed under the skin of the abdomen to deliver medication directly into the intrathecal space. The medication is delivered through a small tube called a catheter that is also surgically placed. The medication can then be administered directly to cells in the spinal cord involved in conveying sensory and motor signals associated with lower urinary tract disorders.

Another system available from Medtronic that is commonly utilized for intrathecal administration is the fully implantable, programmable SynchroMed® Infusion System. The SynchroMed® Infusion System has two parts that are both placed in the body during a surgical procedure: the catheter and the pump. The catheter is a small, soft tube. One end is connected to the catheter port of the pump, and the other end is placed in the intrathecal space. The pump is a round metal device about one inch (2.5 cm) thick, three inches (8.5 cm) in diameter, and weighs about six ounces (205 g) that stores and releases prescribed amounts of medication directly into the intrathecal space. It can be made of titanium, a lightweight, medical-grade metal. The reservoir is the space inside the pump that holds the medication. The fill port is a raised center portion of the pump through which the pump is refilled. The doctor or a nurse inserts a needle through the patient's skin and through the fill port to fill the pump. Some pumps have a side catheter access port that allows the doctor to inject other medications or sterile solutions directly into the catheter, bypassing the pump.

The SynchroMed® pump automatically delivers a controlled amount of medication through the catheter to the intrathecal space around the spinal cord, where it is most effective. The exact dosage, rate and timing prescribed by the doctor are entered in the pump using a programmer, an external computer-like device that controls the pump's memory. Information about the patient's prescription can be stored in the pump's memory. The doctor can easily review this information by using the programmer. The programmer communicates with the pump by radio signals that allow the doctor to tell how the pump is operating at any given time. The doctor also can use the programmer to change your medication dosage.

Methods of intrathecal administration can include those described above available from Medtronic, as well as other methods that are known to one of skill in the art.

Suitable methods for intravesical administration can be found in U.S. Pat. Nos. 6,207,180 and 6,039,967, for example.

For other parenteral administration, the compounds for use in the method of the invention can be formulated for injection or infusion, for example, intravenous, intra-arterial, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents can be used.

Additional Dosage Formulations and Drug Delivery Systems

As compared with traditional drug delivery approaches, some controlled release technologies rely upon the modification of both macromolecules and synthetic small molecules to allow them to be actively instead of passively absorbed into the body. For example, XenoPort Inc. utilizes technology that takes existing molecules and re-engineers them to create new chemical entities (unique molecules) that have improved pharmacologic properties to either: 1) lengthen the short half-life of a drug; 2) overcome poor absorption; and/or 3) deal with poor drug distribution to target tissues. Techniques to lengthen the short half-life of a drug include the use of prodrugs with slow cleavage rates to release drugs over time or that engage transporters in small and large intestines to allow the use of oral sustained delivery systems, as well as drugs that engage active transport systems. Examples of such controlled release formulations, tablets, dosage forms, and drug delivery systems, and that are suitable for use with the present invention, are described in the following published US and PCT patent applications assigned to Xenoport Inc.: US20030158254; US20030158089; US20030017964; US2003130246; WO02100172; WO02100392; WO02100347; WO02100344; WO0242414; WO0228881; WO0228882; WO0244324; WO0232376; WO0228883; and WO0228411. In particular, Xenoport's XP 13512 is a transported Prodrug of gabapentin that has been engineered to utilize high capacity transport mechanisms located in both the small and large intestine and to rapidly convert to gabapentin once in the body. In contrast to gabapentin itself, XP13512 was shown in preclinical and clinical studies to produce dose proportional blood levels of gabapentin across a broad range of oral doses, and to be absorbed efficiently from the large intestine.

Some other controlled release technologies rely upon methods that promote or enhance gastric retention, such as those developed by Depomed Inc. Because many drugs are best absorbed in the stomach and upper portions of the small intestine, Depomed has developed tablets that swell in the stomach during the postprandial or fed mode so that they are treated like undigested food. These tablets therefore sit safely and neutrally in the stomach for 6, 8, or more hours and deliver drug at a desired rate and time to upper gastrointestinal sites. Specific technologies in this area include: 1) tablets that slowly erode in gastric fluids to deliver drugs at almost a constant rate (particularly useful for highly insoluble drugs); 2) bi-layer tablets that combine drugs with different characteristics into a single table (such as a highly insoluble drug in an erosion layer and a soluble drug in a diffusion layer for sustained release of both); and 3) combination tablets that can either deliver drugs simultaneously or in sequence over a desired period of time (including an initial burst of a fast acting drug followed by slow and sustained delivery of another drug). Examples of such controlled release formulations that are suitable for use with the present invention and that rely upon gastric retention during the postprandial or fed mode, include tablets, dosage forms, and drug delivery systems in the following US patents assigned to Depomed Inc.: U.S. Pat. Nos. 6,488,962; 6,451,808; 6,340,475; 5,972,389; 5,582,837; and 5,007,790. Examples of such controlled release formulations that are suitable for use with the present invention and that rely upon gastric retention during the postprandial or fed mode, include tablets, dosage forms, and drug delivery systems in the following published US and PCT patent applications assigned to Depomed Inc.: US20030147952; US20030104062; US20030104053; US20030104052; US20030091630; US20030044466; US20030039688; US20020051820; WO0335040; WO0335039; WO0156544; WO0132217; WO9855107; WO9747285; and WO9318755.

Other controlled release systems include those developed by ALZA Corporation based upon: 1) osmotic technology for oral delivery; 2) transdermal delivery via patches; 3) liposomal delivery via intravenous injection; 4) osmotic technology for long-term delivery via implants; and 5) depot technology designed to deliver agents for periods of days to a month. ALZA oral delivery systems include those that employ osmosis to provide precise, controlled drug delivery for up to 24 hours for both poorly soluble and highly soluble drugs, as well as those that deliver high drug doses meeting high drug loading requirements. ALZA controlled transdermal delivery systems provide drug delivery through intact skin for as long as one week with a single application to improve drug absorption and deliver constant amounts of drug into the bloodstream over time. ALZA liposomal delivery systems involve lipid nanoparticles that evade recognition by the immune system because of their unique polyethylene glycol (PEG) coating, allowing the precise delivery of drugs to disease-specific areas of the body. ALZA also has developed osmotically driven systems to enable the continuous delivery of small drugs, peptides, proteins, DNA and other bioactive macromolecules for up to one year for systemic or tissue-specific therapy. Finally, ALZA depot injection therapy is designed to deliver biopharmaceutical agents and small molecules for periods of days to a month using a nonaqueous polymer solution for the stabilization of macromolecules and a unique delivery profile.

Examples of controlled release formulations, tablets, dosage forms, and drug delivery systems that are suitable for use with the present invention are described in the following US patents assigned to ALZA Corporation: U.S. Pat. Nos. 4,367,741; 4,402,695; 4,418,038; 4,434,153; 4,439,199; 4,450,198; 4,455,142; 4,455,144; 4,484,923; 4,486,193; 4,489,197; 4,511,353; 4,519,801; 4,526,578; 4,526,933; 4,534,757; 4,553,973; 4,559,222; 4,564,364; 4,578,075; 4,588,580; 4,610,686; 4,612,008; 4,618,487; 4,627,851; 4,629,449; 4,642,233; 4,649,043; 4,650,484; 4,659,558; 4,661,105; 4,662,880; 4,675,174; 4,681,583; 4,684,524; 4,692,336; 4,693,895; 4,704,119; 4,705,515; 4,717,566; 4,721,613; 4,723,957; 4,725,272; 4,728,498; 4,743,248; 4,747,847; 4,751,071; 4,753,802; 4,755,180; 4,756,314; 4,764,380; 4,773,907; 4,777,049; 4,781,924; 4,783,337; 4,786,503; 4,788,062; 4,810,502; 4,812,313; 4,816,258; 4,824,675; 4,834,979; 4,837,027; 4,842,867; 4,846,826; 4,847,093; 4,849,226; 4,851,229; 4,851,231; 4,851,232; 4,853,229; 4,857,330; 4,859,470; 4,863,456; 4,863,744; 4,865,598; 4,867,969; 4,871,548; 4,872,873; 4,874,388; 4,876,093; 4,892,778; 4,902,514; 4,904,474; 4,913,903; 4,915,949; 4,915,952; 4,917,895; 4,931,285; 4,946,685; 4,948,592; 4,954,344; 4,957,494; 4,960,416; 4,961,931; 4,961,932; 4,963,141; 4,966,769; 4,971,790; 4,976,966; 4,986,987; 5,006,346; 5,017,381; 5,019,397; 5,023,076; 5,023,088; 5,024,842; 5,028,434; 5,030,454; 5,071,656; 5,077,054; 5,082,668; 5,104,390; 5,110,597; 5,122,128; 5,125,894; 5,141,750; 5,141,752; 5,156,850; 5,160,743; 5,160,744; 5,169,382; 5,171,576; 5,176,665; 5,185,158; 5,190,765; 5,198,223; 5,198,229; 5,200,195; 5,200,196; 5,204,116; 5,208,037; 5,209,746; 5,221,254; 5,221,278; 5,229,133; 5,232,438; 5,232,705; 5,236,689; 5,236,714; 5,240,713; 5,246,710; 5,246,711; 5,252,338; 5,254,349; 5,266,332; 5,273,752; 5,284,660; 5,286,491; 5,308,348; 5,318,558; 5,320,850; 5,322,502; 5,326,571; 5,330,762; 5,338,550; 5,340,590; 5,342,623; 5,344,656; 5,348,746; 5,358,721; 5,364,630; 5,376,377; 5,391,381; 5,402,777; 5,403,275; 5,411,740; 5,417,675; 5,417,676; 5,417,682; 5,423,739; 5,424,289; 5,431,919; 5,443,442; 5,443,459; 5,443,461; 5,456,679; 5,460,826; 5,462,741; 5,462,745; 5,489,281; 5,499,979; 5,500,222; 5,512,293; 5,512,299; 5,529,787; 5,531,736; 5,532,003; 5,533,971; 5,534,263; 5,540,912; 5,543,156; 5,571,525; 5,573,503; 5,591,124; 5,593,695; 5,595,759; 5,603,954; 5,607,696; 5,609,885; 5,614,211; 5,614,578; 5,620,705; 5,620,708; 5,622,530; 5,622,944; 5,633,011; 5,639,477; 5,660,861; 5,667,804; 5,667,805; 5,674,895; 5,688,518; 5,698,224; 5,702,725; 5,702,727; 5,707,663; 5,713,852; 5,718,700; 5,736,580; 5,770,227; 5,780,058; 5,783,213; 5,785,994; 5,795,591; 5,811,465; 5,817,624; 5,824,340; 5,830,501; 5,830,502; 5,840,754; 5,858,407; 5,861,439; 5,863,558; 5,876,750; 5,883,135; 5,840,754; 5,897,878; 5,904,934; 5,904,935; 5,906,832; 5,912,268; 5,914,131; 5,916,582; 5,932,547; 5,938,654; 5,941,844; 5,955,103; 5,972,369; 5,972,370; 5,972,379; 5,980,943; 5,981,489; 5,983,130; 5,989,590; 5,995,869; 5,997,902; 6,001,390; 6,004,309; 6,004,578; 6,008,187; 6,020,000; 6,034,101; 6,036,973; 6,039,977; 6,057,374; 6,066,619; 6,068,850; 6,077,538; 6,083,190; 6,096,339; 6,106,845; 6,110,499; 6,120,798; 6,120,803; 6,124,261; 6,124,355; 6,130,200; 6,146,662; 6,153,678; 6,174,547; 6,183,466; 6,203,817; 6,210,712; 6,210,713; 6,224,907; 6,235,712; 6,245,357; 6,262,115; 6,264,990; 6,267,984; 6,287,598; 6,289,241; 6,331,311; 6,333,050; 6,342,249; 6,346,270; 6,365,183; 6,368,626; 6,387,403; 6,419,952; 6,440,457; 6,468,961; 6,491,683; 6,512,010; 6,514,530; 6,534,089; 6,544,252; 6,548,083; 6,551,613; 6,572,879; and 6,596,314.

Other examples of controlled release formulations, tablets, dosage forms, and drug delivery systems that are suitable for use with the present invention are described in the following published US patent application and PCT applications assigned to ALZA Corporation: US20010051183; WO0004886; WO0013663; WO0013674; WO0025753; WO0025790; WO0035419; WO0038650; WO0040218; WO0045790; WO0066126; WO0074650; WO0119337; WO0119352; WO0121211; WO0137815; WO0141742; WO0143721; WO0156543; WO3041684; WO3041685; WO3041757; WO3045352; WO03051341; WO03053400; WO03053401; WO9000416; WO9004965; WO9113613; WO9116884; WO9204011; WO9211843; WO9212692; WO9213521; WO9217239; WO9218102; WO9300071; WO9305843; WO9306819; WO9314813; WO9319739; WO9320127; WO9320134; WO9407562; WO9408572; WO9416699; WO9421262; WO9427587; WO9427589; WO9503823; WO9519174; WO9529665; WO9600065; WO9613248; WO9625922; WO9637202; WO9640049; WO9640050; WO9640139; WO9640364; WO9640365; WO9703634; WO9800158; WO9802169; WO9814168; WO9816250; WO9817315; WO9827962; WO9827963; WO9843611; WO9907342; WO9912526; WO9912527; WO9918159; WO9929297; WO9929348; WO9932096; WO9932153; WO9948494; WO9956730; WO9958115; and WO9962496.

Another drug delivery technology suitable for use in the present invention is that disclosed by DepoMed, Inc. in U.S. Pat. No. 6,682,759, which discloses a method for manufacturing a pharmaceutical tablet for oral administration combining both immediate-release and prolonged-release modes of drug delivery. The tablet according to the method comprises a prolonged-release drug core and an immediate-release drug coating or layer, which can be insoluble or sparingly soluble in water. The method limits the drug particle diameter in the immediate-release coating or layer to 10 microns or less. The coating or layer is either the particles themselves, applied as an aqueous suspension, or a solid composition that contains the drug particles incorporated in a solid material that disintegrates rapidly in gastric fluid.

Andrx Corporation has also developed drug delivery technology suitable for use in the present invention that includes: 1) a pelletized pulsatile delivery system ("PPDS"); 2) a single composition osmotic tablet system ("SCOT"); 3) a solubility modulating hydrogel system ("SMHS"); 4) a delayed pulsatile hydrogel system ("DPHS"); 5) a stabilized pellet delivery system ("SPDS"); 6) a granulated modulating hydrogel system ("GMHS"); 7) a pelletized tablet system ("PELTAB"); 8) a porous tablet system ("PORTAB"); and 9) a stabilized tablet delivery system ("STDS"). PPDS uses pellets that are coated with specific polymers and agents to control the release rate of the microencapsulated drug and is designed for use with drugs that require a pulsed release. SCOT utilizes various osmotic modulating agents as well as polymer coatings to provide a zero-order drug release.

SMHS utilizes a hydrogel-based dosage system that avoids the "initial burst effect" commonly observed with other sustained-release hydrogel formulations and that provides for sustained release without the need to use special coatings or structures that add to the cost of manufacturing. DPHS is designed for use with hydrogel matrix products characterized by an initial zero-order drug release followed by a rapid release that is achieved by the blending of selected hydrogel polymers to achieve a delayed pulse. SPDS incorporates a pellet core of drug and protective polymer outer layer, and is designed specifically for unstable drugs, while GMHS incorporates hydrogel and binding polymers with the drug and forms granules that are pressed into tablet form. PELTAB provides controlled release by using a water insoluble polymer to coat discrete drug crystals or pellets to enable them to resist the action of fluids in the gastrointestinal tract, and these coated pellets are then compressed into tablets. PORTAB provides controlled release by incorporating an osmotic core with a continuous polymer coating and a water soluble component that expands the core and creates microporous channels through which drug is released. Finally, STDS includes a dual layer coating technique that avoids the need to use a coating layer to separate the enteric coating layer from the omeprazole core.

Examples of controlled release formulations, tablets, dosage forms, and drug delivery systems that are suitable for use with the present invention are described in the following US patents assigned to Andrx Corporation: U.S. Pat. Nos. 5,397,574; 5,419,917; 5,458,887; 5,458,888; 5,472,708; 5,508,040; 5,558,879; 5,567,441; 5,654,005; 5,728,402; 5,736,159; 5,830,503; 5,834,023; 5,837,379; 5,916,595; 5,922,352; 6,099,859; 6,099,862; 6,103,263; 6,106,862; 6,156,342; 6,177,102; 6,197,347; 6,210,716; 6,238,703; 6,270,805; 6,284,275; 6,485,748; 6,495,162; 6,524,620; 6,544,556; 6,589,553; 6,602,522; and 6,610,326.

Examples of controlled release formulations, tablets, dosage forms, and drug delivery systems that are suitable for use with the present invention are described in the following published US and PCT patent applications assigned to Andrx Corporation: US20010024659; US20020115718; US20020156066; WO0004883; WO0009091; WO0012097; WO0027370; WO0050010; WO0132161; WO0134123; WO0236077; WO0236100; WO02062299; WO02062824; WO02065991; WO02069888; WO02074285; WO03000177; WO9521607; WO9629992; WO9633700; WO9640080; WO9748386; WO9833488; WO9833489; WO9930692; WO9947125; and WO9961005.

Some other examples of drug delivery approaches focus on non-oral drug delivery, providing parenteral, transmucosal, and topical delivery of proteins, peptides, and small molecules. For example, the Atrigel® drug delivery system marketed by Atrix Laboratories Inc. comprises biodegradable polymers, similar to those used in biodegradable sutures, dissolved in biocompatible carriers. These pharmaceuticals may be blended into a liquid delivery system at the time of manufacturing or, depending upon the product, may be added later by a physician at the time of use. Injection of the liquid product subcutaneously or intramuscularly through a small gauge needle, or placement into accessible tissue sites through a cannula, causes displacement of the carrier with water in the tissue fluids, and a subsequent precipitate to form from the polymer into a solid film or implant. The drug encapsulated within the implant is then released in a controlled manner as the polymer matrix biodegrades over a period ranging from days to months. Examples of such drug delivery systems include Atrix's Eligard®, Atridox®/Doxirobe®, Atrisorb® FreeFlow™/ Atrisorb®-D FreeFlow, bone growth products, and others as described in the following published U.S. and PCT patent applications assigned to Atrix Laboratories Inc.: US RE37950; U.S. Pat. Nos. 6,630,155; 6,566,144; 6,610,252; 6,565,874; 6,528,080; 6,461,631; 6,395,293; 6,261,583; 6,143,314; 6,120,789; 6,071,530; 5,990,194; 5,945,115; 5,888,533; 5,792,469; 5,780,044; 5,759,563; 5,744,153; 5,739,176; 5,736,152; 5,733,950; 5,702,716; 5,681,873; 5,660,849; 5,599,552; 5,487,897; 5,368,859; 5,340,849; 5,324,519; 5,278,202; 5,278,201; US20020114737, US20030195489; US20030133964; US20010042317; US20020090398; US20020001608; and US2001042317.

Atrix Laboratories Inc. also markets technology for the non-oral transmucosal delivery of drugs over a time period from minutes to hours. For example, Atrix's BEMA™ (Bioerodible Muco-Adhesive Disc) drug delivery system comprises pre-formed bioerodible discs for local or systemic delivery. Examples of such drug delivery systems include those as described in U.S. Pat. No. 6,245,345. Other drug delivery systems marketed by Atrix Laboratories Inc. focus on topical drug delivery. For example, SMP™ (Solvent Particle System) allows the topical delivery of highly water-insoluble drugs. This product allows for a controlled amount of a dissolved drug to permeate the epidermal layer of the skin by combining the dissolved drug with a microparticle suspension of the drug. The SMP™ system works in stages whereby: 1) the product is applied to the skin surface; 2) the product near follicles concentrates at the skin pore; 3) the drug readily partitions into skin oils; and 4) the drug diffuses throughout the area. By contrast, MCA® (Mucocutaneous Absorption System) is a water-resistant topical gel providing sustained drug delivery. MCA® forms a tenacious film for either wet or dry surfaces where: 1) the product is applied to the skin or mucosal surface; 2) the product forms a tenacious moisture-resistant film; and 3) the adhered film provides sustained release of drug for a period from hours to days. Yet another product, BCP™ (Biocompatible Polymer System) provides a non-cytotoxic gel or liquid that is applied as a protective film for wound healing. Examples of these systems include Orajel®-Ultra Mouth Sore Medicine as well as those as described in the following published US patents and applications assigned to Atrix Laboratories Inc.: U.S. Pat. Nos. 6,537,565; 6,432,415; 6,355,657; 5,962,006; 5,725, 491; 5,722,950; 5,717,030; 5,707,647; 5,632,727; and US20010033853.

Additional formulations and compositions available from Teva Pharmaceutical Industries Ltd., Warner Lambert & Co., and Godecke Aktiengesellshaft that include gabapentin and are useful in the present invention include those as described in the following U.S. patents and published U.S. and PCT patent applications: U.S. Pat. Nos. 6,531,509; 6,255,526; 6,054,482; US2003055109; US2002045662; US2002009115; WO 01/97782; WO 01/97612; EP 2001946364; WO 99/59573; and WO 99/59572.

Additional formulations and compositions that include oxybutynin and are useful in the present invention include those as described in the following US patents and published US and PCT patent applications: U.S. Pat. Nos. 5,834,010; 5,601,839; and 5,164,190.

Topical Formulations

Topical formulations can be in any form suitable for application to the body surface, and may comprise, for example, an ointment, cream, gel, lotion, solution, paste or the like, and/or may be prepared so as to contain liposomes, micelles, and/or microspheres. Preferred topical formulations herein are ointments, creams and gels.

Ointments, as is well known in the art of pharmaceutical formulation, are semisolid preparations that are typically based on petrolatum or other petroleum derivatives. The specific ointment base to be used, preferably provides for optimum drug delivery, and, preferably, will provides for other desired characteristics as well, e.g., emolliency or the like. The ointment base is preferably inert, stable, nonirritating and nonsensitizing. As explained in Remington: The Science and Practice of Pharmacy, supra, ointment bases can be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight (See, e.g., Remington: The Science and Practice of Pharmacy, supra).

Creams, as also well known in the art, are viscous liquids or semisolid emulsions, either oil-in-water or water-in-oil. Cream bases are water-washable, and contain an oil phase, an emulsifier and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant.

As will be appreciated by those working in the field of pharmaceutical formulation, gels-are semisolid, suspension-type systems. Single-phase gels contain organic macromolecules distributed substantially uniformly throughout the carrier liquid, which is typically aqueous, but also, preferably, contain an alcohol and, optionally, an oil. Preferred "organic macromolecules," i.e., gelling agents, are crosslinked acrylic acid polymers such as the "carbomer" family of polymers, e.g., carboxypolyalkylenes that may be obtained commercially under the Carbopol® trademark. Also preferred are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methylcellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

Various additives, known to those skilled in the art, may be included in the topical formulations. For example, solubilizers may be used to solubilize certain active agents. For those drugs having an unusually low rate of permeation through the skin or mucosal tissue, it may be desirable to include a permeation enhancer in the formulation; suitable enhancers are as described elsewhere herein.

Transdermal Administration

The compounds of the invention may also be administered through the skin or mucosal tissue using conventional transdermal drug delivery systems, wherein the agent is contained within a laminated structure (typically referred to as a transdermal "patch") that serves as a drug delivery device to be affixed to the skin. Transdermal drug delivery may involve passive diffusion or it may be facilitated using electrotransport, e.g., iontophoresis. In a typical transdermal "patch," the drug composition is contained in a layer, or "reservoir," underlying an upper backing layer. The laminated structure may contain a single reservoir, or it may contain multiple reservoirs. In one type of patch, referred to as a "monolithic" system, the reservoir is comprised of a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are separate and distinct layers, with the adhesive underlying the reservoir which, in this case, may be either a polymeric matrix as described above, or it may be a liquid or hydrogel reservoir, or may take some other form.

The backing layer in these laminates, which serves as the upper surface of the device, functions as the primary structural element of the laminated structure and provides the device with much of its flexibility. The material selected for the backing material should be selected so that it is substantially impermeable to the active agent and any other materials that are present, the backing is preferably made of a sheet or film of a flexible elastomeric material. Examples of polymers that are suitable for the backing layer include polyethylene, polypropylene, polyesters, and the like.

During storage and prior to use, the laminated structure includes a release liner. Immediately prior to use, this layer is removed from the device to expose the basal surface thereof, either the drug reservoir or a separate contact adhesive layer, so that the system may be affixed to the skin. The release liner should be made from a drug/vehicle impermeable material.

Transdermal drug delivery systems may in addition contain a skin permeation enhancer. That is, because the inherent permeability of the skin to some drugs may be too low to allow therapeutic levels of the drug to pass through a reasonably sized area of unbroken skin, it is necessary to coadminister a skin permeation enhancer with such drugs. Suitable enhancers are well known in the art and include, for example, those enhancers listed above in transmucosal compositions.

The formulations of the present invention can be, but are not limited to, short-term, rapid-offset, controlled, for example, sustained release, delayed release and pulsatile release formulations.

The term sustained release is used in its conventional sense to refer to a drug formulation that provides for gradual release of a drug over an extended period of time, and that preferably, although not necessarily, results in substantially constant blood levels of a drug over an extended time period. The period of time can be as long as a month or more and should be a release which is longer that the same amount of agent administered in bolus form.

For sustained release, the compounds can be formulated with a suitable polymer or hydrophobic material which provides sustained release properties to the compounds. As such, the compounds for use the method of the invention can be administered in the form of microparticles for example, by injection or in the form of wafers or discs by implantation.

The term delayed release is used herein in its conventional sense to refer to a drug formulation that provides for an initial release of the drug after some delay following drug administration and that preferably, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes after drug administration.

Coadministration

In practicing the methods of the invention, coadministration refers to administration of a first amount of a 5-HT$_3$ receptor antagonist compound and a second amount of a NARI compound to treat a lower urinary tract disorder. Coadministration encompasses administration of the first and second amounts of the compounds of the coadministration in an essentially simultaneous manner, such as in a single pharmaceutical composition, for example, capsule or tablet having a fixed ratio of first and second amounts, or in multiple, separate capsules or tablets for each. In addition, such coadministration also encompasses use of each compound in a sequential manner in either order. When coadministration involves the separate administration of the NARI and 5-HT$_3$ receptor antagonist, the compounds are administered sufficiently close in time to have the desired therapeutic effect.

Dosing

The therapeutically effective amount or dose of (a) a compound having dual therapeutic modes of action (i.e., 5-HT$_3$ receptor antagonist activity and NARI activity) or (b) a 5-HT$_3$ receptor antagonist and NARI in combination will depend on the age, sex and weight of the patient, the current medical condition of the patient and the nature of the lower urinary tract disorder being treated. The skilled artisan will be able to determine appropriate dosages depending on these and other factors.

As used herein, continuous dosing refers to the chronic administration of a selected active agent.

As used herein, as-needed dosing, also known as "pro re nata" "prn" dosing, and "on demand" dosing or administration is meant the administration of a therapeutically effective dose of the compound(s) at some time prior to commencement of an activity wherein suppression of a lower urinary tract disorder would be desirable. Administration can be immediately prior to such an activity, including about 0 minutes, about 10 minutes, about 20 minutes, about 30 minutes, about 1 hour, about 2 hours, about 3 hours, about 4 hours, about 5 hours, about 6 hours, about 7 hours, about 8 hours, about 9 hours, or about 10 hours prior to such an activity, depending on the formulation.

In a particular embodiment, drug administration or dosing is on an as-needed basis, and does not involve chronic drug administration. With an immediate release dosage form, as-needed administration can involve drug administration immediately prior to commencement of an activity wherein suppression of the symptoms of overactive bladder would be desirable, but will generally be in the range of from about 0 minutes to about 10 hours prior to such an activity, preferably in the range of from about 0 minutes to about 5 hours prior to such an activity, most preferably in the range of from about 0 minutes to about 3 hours prior to such an activity.

A suitable dose of the 5-HT$_3$ receptor antagonist can be in the range of from about 0.001 mg to about 500 mg per day, such as from about 0.01 mg to about 100 mg, for example, from about 0.05 mg to about 50 mg, such as about 0.5 mg to about 25 mg per day. The dose can be administered in a single dosage or in multiple dosages, for example from 1 to 4 or more times per day. When multiple dosages are used, the amount of each dosage can be the same or different.

A suitable dose of the NARI compound can be in the range of from about 0.001 mg to about 1000 mg per day, such as from about 0.05 mg to about 500 mg, for example, from about 0.03 mg to about 300 mg, such as about 0.02 mg to about 200 mg per day. The dose can be administered in a single dosage or in multiple dosages, for example from 1 to 4 or more times per day. When multiple dosages are used, the amount of each dosage can be the same or different.

A suitable dose of the compound having both 5-HT$_3$ receptor antagonist and NARI activity can be in the range of from about 0.001 mg to about 1000 mg per day, such as from about 0.05 mg to about 500 mg, for example, from about 0.03 mg to about 300 mg, such as from about 0.02 mg to about 200 mg per day. In a particular embodiment, a suitable dose of the compound having both 5-HT$_3$ receptor antagonist and NARI activity can be in the range of from about 0.1 mg to about 50 mg per day, such as from about 0.5 mg to about 10 mg per, day such as about 0.5, 1, 2, 3, 4, 5, 6, 7, 8, 9, or 10 mg per day. The dose per day can be administered in a single dosage or in multiple dosages, for example from 1 to 4 or more times per day. When multiple dosages are used, the amount of each dosage can be the same or different. For example a dose of 1 mg per day can be administered as two 0.5 mg doses, with about a 12 hour interval between doses.

It is understood that the amount of compound dosed per day can be administered every day, every other day, every 2 days, every 3 days, every 4 days, every 5 days, etc. For example, with every other day administration, a 5 mg per day dose can be initiated on Monday with a first subsequent 5 mg per day dose administered on Wednesday, a second subsequent 5 mg per day dose administered on Friday, etc.

The compounds for use in the method of the invention can be formulated in unit dosage form. The term "unit dosage form" refers to physically discrete units suitable as unitary dosage for subjects undergoing treatment, with each unit containing a predetermined quantity of active material calculated to produce the desired therapeutic effect, optionally in association with a suitable pharmaceutical carrier. The unit dosage form can be for a single daily dose or one of multiple daily doses (e.g., about 1 to 4 or more times per day). When multiple daily doses are used, the unit dosage form can be the same or different for each dose.

For the compounds having both NARI and 5-HT$_3$ receptor antagonist activity, each dosage can typically contain from about 0.001 mg to about 1000 mg, such as from about 0.05 mg to about 500 mg, for example, from about 0.03 mg to about 300 mg, such as about 0.02 mg to about 200 mg of the active ingredient.

When the method of treatment comprises coadministration of a NARI and a 5-HT$_3$ receptor antagonist each dose can typically contain from about 0.001 mg to about 1000 mg, such as from about 0.05 mg to about 500 mg, for example, from about 0.03 mg to about 300 mg, such as about 0.02 mg to about to about 200 mg of the NARI and typically can contain from about 0.001 mg to about 500 mg, such as from about 0.01 mg to about 100 mg, for example, from about 0.05 mg to about 50 mg, such as about 0.5 mg to about 25 mg of the 5-HT$_3$ receptor antagonist.

The invention further includes a kit for treating at least one symptom of a lower urinary tract disorder in a subject in need of treatment, wherein the symptom is selected from the group consisting of urinary frequency, urinary urgency, urge incontinence, nocturia and enuresis. The kit comprises a compound having 5-HT$_3$ receptor antagonist activity and instructions for use with a compound having NARI activity, according to the method of the invention.

The invention further includes a kit for treating at least one symptom of a lower urinary tract disorder in a subject in need of treatment, wherein the symptom is selected from the group consisting of urinary frequency, urinary urgency, urge incontinence, nocturia and enuresis. The kit comprises a compound having NARI activity and instructions for use with a compound having 5-HT$_3$ receptor antagonist activity, according to the method of the invention.

The invention further includes a kit for treating at least one symptom of a lower urinary tract disorder in a subject in need of treatment, wherein the symptom is selected from the group consisting of urinary frequency, urinary urgency, urge incontinence, nocturia and enuresis. The kit comprises at least one compound having both 5-HT$_3$ receptor antagonist activity and NARI activity (i.e., a single compound) and an instructional insert for administering the compound, according to the method of the invention. In another embodiment, the kit can comprise a first compound which has 5-HT$_3$ receptor antagonist activity and a second compound having NARI activity and an instructional insert for administering the first and second compounds, according to the method of the invention.

Compounds can be in separate dosage forms or combined in a single dosage form. In other embodiments of the kits, the instructional insert further includes instructions for administration with an additional therapeutic agent as described herein.

It is understood that in practicing the method or using a kit of the present invention that administration encompasses administration by different individuals (e.g., the subject, physicians or other medical professionals) administering the same or different compounds.

As used herein, the term pharmaceutically acceptable salt refers to a salt of the administered compounds prepared from pharmaceutically acceptable non-toxic acids including inorganic acids, organic acids, solvates, hydrates, or clathrates thereof. Examples of such inorganic acids are hydrochloric, hydrobromic, hydroiodic, nitric, sulfuric, and phosphoric. Appropriate organic acids may be selected, for example, from aliphatic, aromatic, carboxylic and sulfonic classes of organic acids, examples of which are formic, acetic, propionic, succinic, camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic (besylate), stearic, sulfanilic, alginic, galacturonic, and the like.

It is understood that 5-HT$_3$ receptor antagonists, NARIs and single compounds having both NARI and 5-HT$_3$ antagonist activities can be identified, for example, by screening libraries or collections of molecules using suitable methods. Another source for the compounds of interest are combinatorial libraries which can comprise many structurally distinct molecular species. Combinatorial libraries can be used to identify lead compounds or to optimize a previously identified lead. Such libraries can be manufactured by well-known methods of combinatorial chemistry and screened by suitable methods.

The invention also relates to a method of processing a claim under a health insurance policy submitted by a claimant seeking reimbursement for costs associated with the treatment of a functional bowel disorder as described herein.

In one embodiment, the method for processing a claim under a health insurance policy submitted by a claimant seeking reimbursement for costs associated with treatment of at least one symptom of a lower urinary tract disorder wherein, said treatment comprises coadministering to a subject a first amount of a 5-HT$_3$ receptor antagonist and a second amount of a noradrenaline reuptake inhibitor, wherein the first and second amounts together comprise a therapeutically effective amount comprising: reviewing said claim; determining whether said treatment is reimbursable under said insurance policy; and processing said claim to provide partial or complete reimbursement of said costs.

In one embodiment, the lower urinary tract disorder being treated is selected from the group consisting of overactive bladder, interstitial cystitis, prostatitis, prostadynia and benign prostatic hyperplasia.

In another embodiment, the lower urinary tract disorder is overactive bladder.

In yet another embodiment, the lower urinary tract disorder is interstitial cystitis.

The invention also relates to a method for processing a claim under a health insurance policy submitted by a claimant seeking reimbursement for costs associated with treatment of at least one symptom of a lower urinary tract disorder wherein, said treatment comprises coadministering to a subject a therapeutically effective amount of a 5-HT$_3$ receptor antagonist and a therapeutically effective amount of a noradrenaline reuptake inhibitor comprising: reviewing said claim; determining whether said treatment is reimbursable under said insurance policy; and processing said claim to provide partial or complete reimbursement of said costs.

In one embodiment, the lower urinary tract disorder being treated is selected from the group consisting of overactive bladder, interstitial cystitis, prostatitis, prostadynia and benign prostatic hyperplasia.

In another embodiment, the lower urinary tract disorder is overactive bladder.

In yet another embodiment, the lower urinary tract disorder is interstitial cystitis.

The invention further relates to a method for processing a claim under a health insurance policy submitted by a claimant seeking reimbursement for costs associated with treatment of at least one symptom of a lower urinary tract disorder wherein, said treatment comprises administering to a subject a therapeutically effective amount of a compound having 5-HT$_3$ receptor antagonist activity and noradrenaline reuptake inhibitor acitivity comprising: reviewing said claim; determining whether said treatment is reimbursable under said insurance policy; and processing said claim to provide partial or complete reimbursement of said costs.

In a particular embodiment the compound having 5-HT$_3$ receptor antagonist activity and noradrenaline reuptake inhibitor acitivity is MCI-225.

In one embodiment, the lower urinary tract disorder being treated is selected from the group consisting of overactive bladder, interstitial cystitis, prostatitis, prostadynia and benign prostatic hyperplasia.

In another embodiment, the lower urinary tract disorder is overactive bladder.

In yet another embodiment, the lower urinary tract disorder is interstitial cystitis.

Pharmacological Methods

Acute Models: Dilute Acetic Acid Model and Protamine Sulfate/Physiological Urinary Potassium Model The acute models described below provide methods for evaluating active agents in the treatment of overactive bladder. Briefly, the models provide a method for reducing the bladder capacity of test animals by infusing either protamine sulfate and potassium chloride (See, Chuang, Y. C. et al., Urology 61(3): 664–670 (2003)) or dilute acetic acid (See, Sasaki, K. et al., J. Urol. 168(3): 1259–1264 (2002)) into the bladder. The infusates cause irritation of the bladder and a reduction in bladder capacity by selectively activating bladder afferent fibers, such as C-fiber afferents. Following irritation of the bladder, an active agent (drug) can be administered and the ability of the active agent to reverse (partially or totally) the reduction in bladder capacity resulting from the irritation, can be determined. Substances which reverse the reduction in bladder capacity can be used in the treatment of overactive bladder.

Animal Preparation for Acute Models:

Female rats (250–275 g BW) are anesthetized with urethane (1.2 g/kg) and a saline-filled jugular catheter (PE-50) is inserted for intravenous drug administration and a heparinized (100 units/ml) saline-filled carotid catheter (PE-50) is inserted for blood pressure monitoring. Via a midline abdominal incision from xyphoid to navel, a PE-50 catheter is inserted into the bladder dome for bladder filling and pressure recording. The abdominal cavity is moistened with saline and closed by covering with a thin plastic sheet in order to maintain access to the bladder for filling cystometry emptying purposes. Fine silver or stainless steel wire electrodes are inserted into the external urethral sphincter (EUS) percutaneously for electromyography (EMG).

Dilute Acetic Acid Model:

Saline and all subsequent infusates are continuously infused at a rate of about 0.055 ml/min via the bladder filling catheter for 30–60 minutes to obtain a baseline of lower urinary tract activity (continuous cystometry; CMG). Bladder pressure traces act as direct measures of bladder and urethral outlet activity, and EUS-EMG phasic firing and voiding act as indirect measures of lower urinary tract activity during continuous transvesical cystometry. Following the control period, a 0.25% acetic acid solution in saline (AA) is infused into the bladder to induce bladder irritation. Following 30 minutes of AA infusion, 3 vehicle injections are made at 20 minute intervals to determine vehicle effects, if any. Subsequently, increasing doses of a selected active agent are administered intravenously at 30 minute intervals in order to construct a cumulative dose-response relationship. At the end of the control saline cystometry period, the third vehicle injection, and 20 minutes following each subsequent treatment, the infusion pump is stopped, the bladder is emptied by fluid withdrawal via the infusion catheter and a single filling cystometrogram is performed at the same flow rate in order to determine changes in bladder capacity caused by the irritation protocol and subsequent drug administration. In this acute model, C-fiber afferent pathways within the bladder are selectively activated.

Protamine Sulfate/Physiological Urinary Potassium Model:

Saline and all subsequent infusates are continuously infused at a rate of about 0.055 m/min via the bladder filling catheter for about 30–60 minutes to obtain a baseline of lower urinary tract activity (continuous cystometry; CMG). Bladder pressure traces act as direct measures of bladder and urethral outlet activity, and EUS-EMG phasic firing and voiding act as indirect measures of lower urinary tract activity during continuous transvesical cystometry. Following the control period, a 10 mg/mL protamine sulfate (PS) in saline solution is infused for about 30 minutes in order to permeabilize the urothelial diffusion barrier. After PS treatment, the infusate is switched to 300 mM KCl in saline to induce bladder irritation. Once a stable level of lower urinary tract hyperactivity is established (20–30 minutes), 3 vehicle injections are made at about 30 minute intervals to assess the effects of the vehicle. Subsequently, increasing doses of a selected active agent are administered intravenously at about 30 minute intervals in order to construct a cumulative dose-response relationship. At the end of the control saline cystometry period, the third vehicle injection, and 20 minutes following each subsequent treatment, the infusion pump is stopped, the bladder is emptied by fluid withdrawal via the infusion catheter and a single filling cystometrogram is performed at the same flow rate in order to determine changes in bladder capacity caused by the irritation protocol and subsequent drug administration. This model acutely activates bladder afferent fibers, including, C-fiber afferents.

Chronic Model: Chronic Spinal Cord Injury Model

The following is a model of neurogenic bladder, in which C-fiber afferents are chronically activated as a result of spinal cord injury (See, Yoshiyama, M. et al., Urology 54(5): 929–933 (1999)). Following spinal cord injury an active agent (drug) can be administered and the ability of the active agent to reverse (partially or totally) the reduction in bladder capacity resulting from spinal cord injury can be determined. Substances which reverse the reduction in bladder capacity can be used in the treatment of overactive bladder, for example, neurogenic bladder.

Animal Preparation for Chronic Model:

Female Sprague-Dawley rats (Charles River, 250–300 g) are anesthetized with isofluorane (4%) and a laminectomy is performed at the T9-10 spinal level. The spinal cord is transected and the intervening space filled with Gelfoam. The overlying muscle layers and skin are sequentially closed with suture, and the animals are treated with antibiotic (100 mg/kg ampicillin s.c.). Residual urine is expressed prior to returning the animals to their home cages, and thereafter 3 times daily until terminal experimentation four weeks later. On the day of the experiment, the animals are anesthetized with isofluorane (4%) and a jugular catheter (PE10) is inserted for access to the systemic circulation and tunneled subcutaneously to exit through the midscapular region. Via a midline abdominal incision, a PE50 catheter with a fire-flared tip is inserted into the dome of the bladder through a small cystotomy and secured by ligation for bladder filling and pressure recording. Small diameter (75 μm) stainless steel wires are inserted percutaneously into the external urethral sphincter (EUS) for electromyography (EMG). The abdominal wall and the overlying skin of the neck and abdomen are closed with suture and the animal is mounted in a Ballman-type restraint cage. A water bottle is positioned within easy reach of the animal's mouth for ad libitum access to water. The bladder catheter is hooked up to the perfusion pump and pressure transducer, and the EUS-EMG electrodes to their amplifier. Following a 30 minute recovery from anesthesia and acclimatization, normal saline is infused at a constant rate (0.100–0.150 ml/min) for control cystometric recording.

Chronic Spinal Cord Injury Model:

Following a 60–90 minute control period of normal saline infusion (0.100–0.150 ml/min) to collect baseline continuous open cystometric data, the pump is turned off, the bladder is emptied, the pump turned back on, and bladder capacity is estimated by a filling cystometrogram. At 3×20–30 minute intervals, vehicle is administered intravenously in order to ascertain vehicle effects on bladder activity. Following the third vehicle control, bladder capacity is again estimated as described above. Subsequently, a cumulative dose-response is performed with the agent of choice. Bladder capacity is measured 20 minutes following each dose. This is a model of neurogenic bladder, in which C-fiber afferents are chronically activated.

Exemplification

The present invention will now be illustrated by the following Example, which is not intended to be limiting in any way.

Treatment of Overactive Bladder Using MCI-225

The effect of the administration of MCI-225 was assessed using the Dilute Acetic Acid Model. Specifically, the ability of MCI-225 to reverse the irritation-induced reduction in bladder capacity caused by continuous intravesical infusion of dilute acetic acid was assessed.

Dilute Acetic Acid Model-Rats

Female rats (250–275 g BW, n=8) were anesthetized with urethane (1.2 g/kg) and a saline-filled catheter (PE-50) was inserted into the proximal duodenum for intraduodenal drug administration. A flared-tipped PE-50 catheter was inserted into the bladder dome, via a midline lower abdominal incision, for bladder filling and pressure recording and secured by ligation. The abdominal cavity was moistened with saline and closed by covering with a thin plastic sheet in order to maintain access to the bladder for emptying purposes. Fine silver or stainless steel wire electrodes were inserted into the external urethral sphincter (EUS) percutaneously for electromyography (EMG). Animals were positioned on a heating pad which maintained body temperature at 37° C.

Saline and all subsequent infusates were continuously infused at a rate of about 0.055 ml/min via the bladder filling catheter for about 60 minutes to obtain a baseline of lower urinary tract activity (continuous cystometry; CMG). At the end of the control saline cystometry period, the infusion pump was stopped, the bladder was emptied by fluid withdrawal via the infusion catheter and a single filling cystometrogram was performed using saline at the same flow rate as the continuous infusion, in order to measure bladder capacity. Bladder capacity (ml) was calculated as the flow rate of the bladder filling solution (ml/min) multiplied by the elapsed time between commencement of bladder filling and occurrence of bladder contraction (min).

Following the control period, a 0.25% acetic acid solution in saline (AA) was infused into the bladder to induce bladder irritation. Following 30 minutes of AA infusion, 3 vehicle injections (10% TWEEN® 80 in saline, 1 ml/kg dose) were administered intraduodenally at 20 minute intervals to determine vehicle effects on the intercontraction interval and to achieve a stable level of irritation with the dilute acetic acid solution. Following injection of the third vehicle control, bladder capacity was again measured, as described above but using AA to fill the bladder. Increasing doses of MCI-225 (3, 10 or 30 mg/kg, as a 1 ml/kg dose) were then administered intraduodenally at 60 minute intervals in order to construct a cumulative dose-response relationship. Bladder capacity was measured as described above using AA to fill the bladder, at 20 and 50 minutes following each subsequent drug treatment.

Data Analysis:

Bladder capacity was determined for each treatment regimen as described above (flow rate of the bladder filling solution (ml/min) multiplied by the elapsed time between commencement of bladder filling and occurrence of bladder contraction (min)) and converted to % Bladder Capacity normalized to the last vehicle measurement of the AA/Veh 3 treatment group. Data were then analyzed by non-parametric ANOVA for repeated measures (Friedman Test) with Dunn's Multiple Comparison test. All comparisons were made from the last vehicle measurement (AA/Veh 3). The 30 and 60 minute post-drug measures were very similar, so the average of these two measures was used as the effect for each dose. $P<0.050$ was considered significant.

Results:

Intraduodenal MCI-225 resulted in a dose-dependent increase in bladder capacity in the dilute acetic acid model, as measured by filling cystometry in rats (n=8) during continuous irritation. This effect was statistically significant at the dose range of 3–30 mg/kg ($p=0.0005$ by Friedman test), the 10 mg/kg and 30 mg/kg responses were significantly higher than AA/Veh 3 ($p<0.05$ and $p<0.001$ by Dunn's multiple comparison test, respectively). The results are set forth graphically in the FIG. 1 (Sal=saline).

Conclusion:

The ability of MCI-225 to reverse the irritation-induced reduction in bladder capacity suggests both a direct effect of this compound on bladder C-fiber activity via 5-$HT_3$ receptor antagonism and an enhancement of sympathetic inhibition of bladder activity via noradrenaline reuptake inhibition. The effectiveness of MCI-225 in this model is predictive of efficacy in the treatment of lower urinary tract disorders in humans.

Dilute Acetic Acid Model-Cats

The ability of MCI-225 to reverse the reduction in bladder capacity seen following continuous infusion of dilute acetic acid in a cat model, a commonly used model of overactive bladder (Thor and Katofiasc, 1995, *J. Pharmacol. Exptl. Ther.* 274: 1014–24).

Materials and Methods

Six alpha-chloralose anesthetized (50–100 mg/kg) normal female cats (2.5–3.5 kg; Harlan) were utilized in this study.

Drugs and Preparation

MCI-225 was dissolved in 5% methylcellulose in water at 3.0, 10.0 or 30 mg/ml Animals were dosed by volume of injection=body weight in kg.

Acute Anesthetized In vivo Model

Female cats (2.5–3.5 kg; Harlan) had their food removed the night before the study. The following morning, the cats were anesthetized with isoflurane and prepped for surgery using aseptic technique. Polyethylene catheters were surgically placed to permit the measurement of bladder pressure, urethral pressure, arterial pressure, respiratory rate as well as for the delivery of drugs. Fine wire electrodes were implanted alongside the external urethral anal sphincter. Following surgery, the cats were slowly switched from the gas anesthetic isoflurane (2–3.5%) to alpha-chloralose (50–100 mg/kg). During control cystometry, saline was slowly infused into the bladder (0.5–1.0 ml/min) for 1 hour. The control cystometry was followed by 0.5% acetic acid in saline for the duration of the experiment. After assessing the cystometric variables under these baseline conditions, the effects of MCI-225 on bladder capacity were determined via a 3 point dose response protocol.

Data Analysis

Data was analyzed using a non-parametric One-Way ANOVA (Friedman Test) with the post-hoc Dunn's multiple comparison t test. P<0.05 was considered significant.

Results and Conclusions

Figure 2:
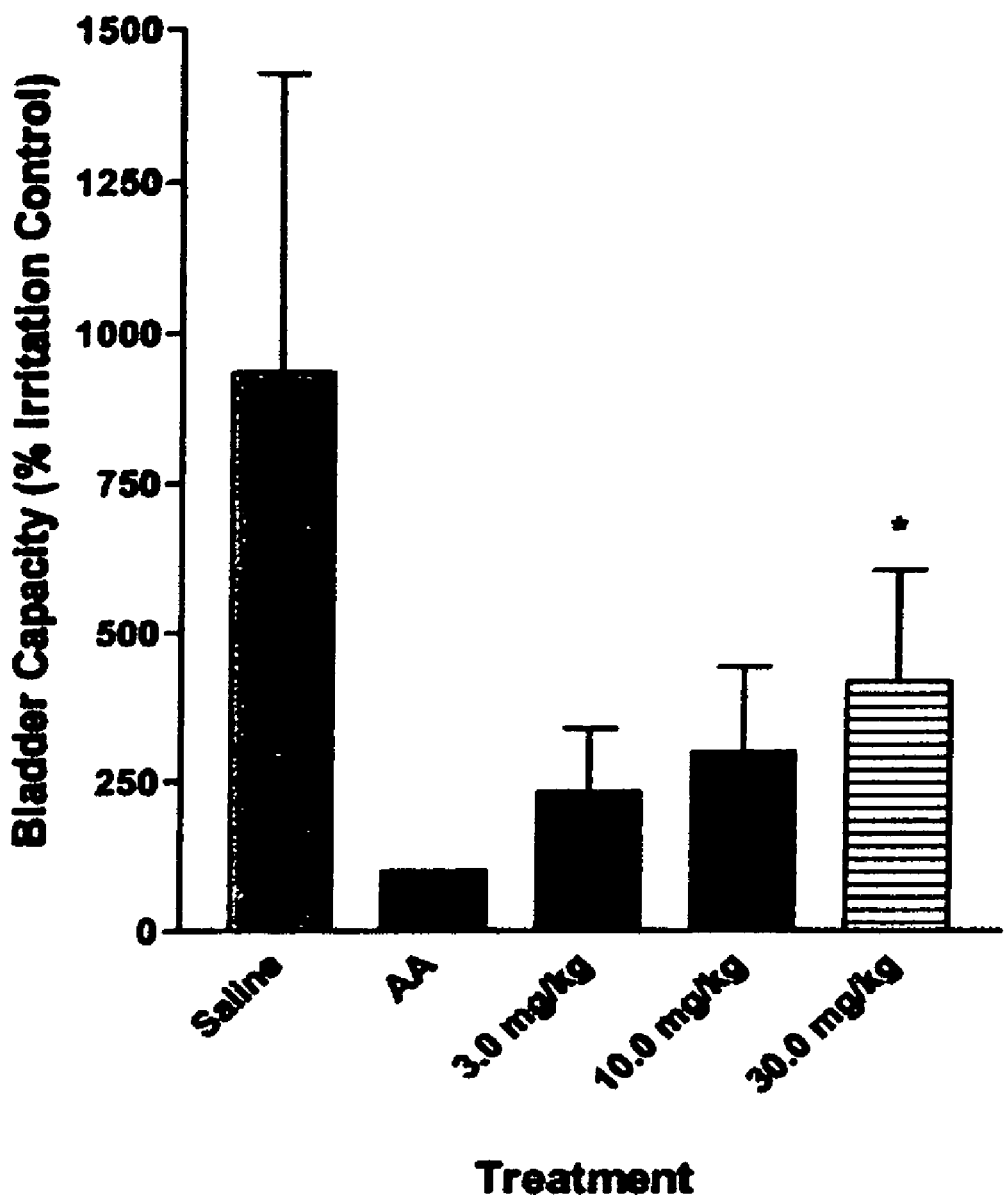
FIG. 2 is a graph of bladder capacity (reported as % Bladder Capacity normalized to the last vehicle treatment measurement of the AA treatment group) for the indicated treatment regimen in cats subjected to the dilute acetic acid model described herein.

MCI-225 caused a significant dose-dependent increase in bladder capacity following acetic acid irritation (P<0.0103), with individual dose significance attained at the 30 mg/kg dose (P<0.05) (FIG. 2). These data support the initial positive findings in the rat, demonstrating that MCI-225 is effective in increasing bladder capacity in commonly utilized models of OAB in two species. These results are also predictive of the efficacy of MCI-225 in the treatment of BPH, for example, the irritative symptoms of BPH.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for treating overactive bladder without involuntary loss of urine comprising administering a therapeutically effective amount of a compound of formula II:

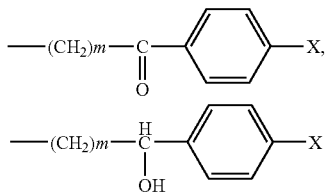

or a pharmaceutically acceptable salt thereof to a human subject in need thereof.

2. The method of claim 1, wherein said administering is oral.

3. The method of claim 1, wherein said administering is on an as-needed basis.

4. The method of claim 1, wherein said therapeutically effective amount is from about 0.001 to about 1000 mg per day.

5. The method of claim 1, wherein said therapeutically effective amount is from about 0.05 to about 500 mg per day.

6. The method of claim 1, wherein said therapeutically effective amount is from about 0.03 to about 300 mg per day.

7. The method of claim 1, wherein said therapeutically effective amount is from about 0.02 to about 200 mg per day.

8. The method of claim 1, wherein said therapeutically effective amount is from about 0.1 to about 50 mg per day.

9. A method for treating at least one symptom of overactive bladder without involuntary loss of urine, wherein the symptom is selected from the group consisting of urinary frequency and urinary urgency, comprising administering a therapeutically effective amount of a compound of formula II:

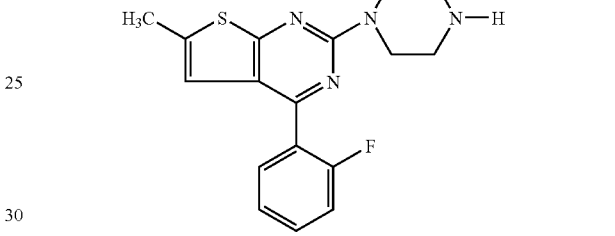

or a pharmaceutically acceptable salt thereof to a human subject in need thereof.

10. The method of claim 9, wherein said administering is oral.

11. The method of claim 9, wherein said administering is on an as-needed basis.

12. The method of claim 9, wherein said therapeutically effective amount is from about 0.001 to about 1000 mg per day.

13. The method of claim 9, wherein said therapeutically effective amount is from about 0.05 to about 500 mg per day.

14. The method of claim 9, wherein said therapeutically effective amount is from about 0.03 to about 300 mg per day.

15. The method of claim 9, wherein said therapeutically effective amount is from about 0.02 to about 200 mg per day.

16. The method of claim 9, wherein said therapeutically effective amount is from about 0.1 to about 50 mg per day.

* * * * *